(12) United States Patent
Sachs

(10) Patent No.: US 6,602,892 B1
(45) Date of Patent: Aug. 5, 2003

(54) METHODS FOR NICOTINE REPLACEMENT DOSAGE DETERMINATION

(76) Inventor: David P. L. Sachs, 3618 Laguna Ave., Palo Alto, CA (US) 94306

( * ) Notice: Subject to any disclaimer, the term of this patent is extended or adjusted under 35 U.S.C. 154(b) by 0 days.

(21) Appl. No.: 08/422,381

(22) Filed: Apr. 13, 1995

Related U.S. Application Data

(63) Continuation-in-part of application No. 08/074,764, filed on Jun. 10, 1993, now abandoned.
(51) Int. Cl.$^7$ .................. A61K 31/44; A01N 25/00; G01N 33/00; G01N 33/53
(52) U.S. Cl. .................. 514/343; 514/813; 436/816; 436/106; 436/901
(58) Field of Search ................. 514/343, 813; 436/816, 106, 901

(56) References Cited

U.S. PATENT DOCUMENTS 4,943,435 A   7/1990   Baker et al. ............. 424/448
5,069,904 A   12/1991  Masterson ............... 424/401

OTHER PUBLICATIONS

DiPiro et al, "Pharmacotherapy; A Pathophysiologic Approach," Elsevier, New York (1989) pp. 15–17.*
Goodman Gilman et al., "The Pharamcological Basis of Therapeutics," (6$^{th}$ Ed.), Macmillan, New York, (1980) pp. 43–48.*
E. Minneker et al. "The Effect of Different Dosages of a Transdermal Nicotine Substitution System on the Success Rate of Smoking Cessation Therapy," Meth and Find Exp Clin Pharmacol (1989); 11(3):219–222.

K. K. H. Chan et al. "Pharmacokinetics of a Single Transdermal Dose of Nicotine in Healthy Smokers," Journal of controlled Release, 14 (1990) 145–151.
H. D. Ross et al. "Pharmacokinetics of Multiple Daily Transdermal Doses of Nicotine in Healthy Smokers," Pharmaceutical Research, (1991) vol. 8, No. 3, 385–388.
G. M. Kochak et al. "Pharmacokinetic Disposition of Multiple–Dose Transdermal Nicotine in Healthy Adult Smokers," Pharmaceutical Research, (1992) vol. 9, No. 11, 1451–1455.
M. C. Fiore, MD et al. "Tobacco Dependence and the Nicotine Patch 'Clinical Guidelines for Effective Use'," JAMA (1992) vol. 268, No. 19, 2687–2694.
D. P. L. Sachs et al. "Effectiveness of a 16–Hour Transdermal Nicotine Patch in a Medical Practice Setting, Without Intensive Group Counseling," Arch Intern Med/vol 153, (1993) 1881–1890.

* cited by examiner

Primary Examiner—Sreeni Padmanabhan
Assistant Examiner—Shenjiun Wang
(74) Attorney, Agent, or Firm—Townsend and Townsend and Crew LLP

(57) ABSTRACT

A method for predicting nicotine replacement dosage to achieve a target nicotine serum concentration relies on measuring blood nicotine concentration prior to smoking cessation. At least two values corresponding to other patient characteristics, such as body mass, cumulative smoking, psychological dependence, age, and menopausal status, are also determined and used to predict expected blood nicotine concentrations based on nicotine replacement dosages. Such methods are useful in achieving target blood nicotine concentrations for smoking cessation and therapy.

10 Claims, 14 Drawing Sheets

METHODS FOR NICOTINE REPLACEMENT DOSAGE DETERMINATION

This application is a continuation-in-part of application Ser. No. 08/074,764, filed on Jun. 10, 1993, now abandoned, the disclosure of which is incorporated herein by reference.

BACKGROUND OF THE INVENTION

1. Field of the Invention

The present invention relates generally to methods for smoking cessation assistance, and more particularly to methods for determining and predicting dosages utilized in nicotine replacement therapy employed in conjunction with smoking cessation techniques.

Cigarette smoking is a serious health concern in the United States and throughout the world, being a significant causative factor in several types of cancer, heart disease, and other disabilities. While the risk of these diseases can be greatly reduced by simply stopping smoking, tobacco dependency makes stopping very difficult for many patients. Thus, there is a continuing need to provide aids for use in smoking cessation therapy.

Of particular interest to the present invention, a number of products have been commercially developed for providing nicotine replacement while a patient is undergoing smoking cessation and may suffer the symptoms of nicotine withdrawal. Such nicotine replacement can be achieved by a variety of products, including gums, transdermal patches, nasal spray, inhalers, lozenges, and the like. Frequently, the use of such nicotine replacement products will be combined with physician counseling, group and/or psychological counseling to further increase the chances of long term sustained abstinence.

While a significant improvement over counseling alone, nicotine replacement therapy is not always successful. Nicotine replacement alone (defined as at least one year of sustained abstinence from smoking) achieves a success rate in the range from 0% to 12%, while nicotine replacement combined with counseling achieves a success in the range from 25% to 38%.

It would therefore be desirable to provide improved methods and therapies for assisting in smoking cessation. It would be particularly desirable to provide methods for further increasing the success of nicotine replacement therapy, both by itself and in combination with other smoking cessation, aids. Such methods should be straightforward and preferably require a minimum of patient follow-up. Such methods should also be efficient, adding little to the cost of therapy while achieving significantly higher compliance rates. These and other objectives will be met, in whole and in part, by the invention of the present application as described in more detail hereinbelow.

2. Description of the Background Art

U.S. Pat. No. 5,069,904, describes nicotine therapy for disease treatment where dosage is determined by incrementally increasing the administered amount until a putative therapeutic dosage is achieved. Nicotine patches intended for delivering safe and steady blood plasma levels of nicotine are described in various patent publications, including U.S. Pat. No. 4,943,435. The pharmacokinetics of nicotine patch replacement is described in various journal publications, including Fiore et al. (1992) J. Am. Med. Assn. 268:2687–2694; Ross et al. (1991) Pharm. Res. 8:385–388; Chan et al. (1990) J. Controlled Release 14:145–151; Kochak et al. (1992) Pharm. Res. 9:1451–1455; and Minneker et al. (1989) Meth. Find. Exp. Clin. Pharmacol. 11:219–222. The Minneker et al. (1989) publication reported that nicotine transdermal replacement dosages adapted to previous daily cigarette consumption was no more effective than a standard dosage for achieving successful smoking cessation therapy.

SUMMARY OF THE INVENTION

The present invention is based on the observation that patient success in smoking cessation therapy correlates strongly with the degree to which the nicotine replacement therapy is able to be achieved in relation to pre-cessation blood levels of nicotine. In particular, it is observed herein that long term patient abstinence is achieved more often in those patients where at least about 40%, usually at least about 50%, of pre-cessation blood nicotine levels (measured as a nicotine metabolite, usually cotinine) are maintained by the replacement therapy. Surprisingly, however, it is also observed herein that nicotine replacement levels of blood cannot be adequately predicted based upon the level of administered dosage alone. That is, blood nicotine levels appear to depend on a number of individual patient factors in addition to the replacement dosage.

Thus, the present invention provides methods for determining nicotine replacement dosages for effective smoking cessation in patients, where an initial nicotine replacement dosage is determined based on a number of patient characteristics selected from the group consisting of a body mass factor, a cumulative smoking factor, a psychological dependence factor, age, and menopausal status. Such dosages are selected to achieve replacement nicotine concentrations in blood meeting a desired threshold amount, typically at least about 50% of the pre-cessation nicotine levels.

The preferred patient characteristics will vary between males and females. For males, the preferred patient characteristics include at least the body mass factor and the cumulative smoking factor. The psychological dependence factor and patient age are also useful, although not as predictive as the body mass factor and cumulative smoking factor. For females, the preferred patient characteristics include at least the psychological dependence factor and age. Menopausal status is also a significant factor, with the body mass factor also being significant, although less so than the previously mentioned factors. The cumulative smoking factor appears to be of little relevance to predicting the relationship between dosage and blood nicotine levels in women.

The present invention also provides a method for determining the relationship between nicotine dosage and nicotine serum levels in a population of patients who smoke tobacco. The method relies on measuring blood nicotine concentrations in individual patients while said patients are smoking. After the patients have stopped smoking, known dosages of nicotine are administered and blood nicotine concentrations measured, while the patient remains abstinent from smoking. At least two values corresponding to the patient characteristics set forth above are determined for each individual patient in the population, and a relationship between the nicotine dosage and nicotine blood concentration as a function of both the blood nicotine concentration while smoking and at least two patient characteristics can then be determined by known mathematical techniques, such as regression analysis.

It is important to reach the target blood nicotine level, delivered by the therapeutic medication, as rapidly as possible after smoking cessation, referred to as the patient's Target Quit Date. If there is delay, and the blood nicotine level is too low, then risk of relapse back to smoking can increase 10-fold in the first day or two after Target Quit Date. Conversely, if the physician initiates treatment with too high a therapeutic nicotine medication dose, then the patient could experience untoward side effects, such as nausea or vomiting, causing the patient to stop medication and likely relapse back to smoking. The present invention allows the physician to start the patient with the proper dose of nicotine replacement medication which individually optimizes that patient's chance of successfully stopping smoking.

The initial dosages predicted by the method of the present invention are often counter-intuitive. For example the method provides for substantially higher nicotine patch doses to achieve adequate nicotine replacement blood level in short, obese men (the prototypical, paunchy beer-bellied man), then in men of average body build. While this finding might make common sense, consider what the method predicts for women: The tall, slender woman—the "ideal" fashion model—also needs a substantially higher nicotine patch dose to receive adequate treatment than does a woman of average body build. Thus, the short, obese man and the tall, slender woman each need high nicotine patch doses, while the tall, thin man, and the short, obese woman each need low nicotine patch doses to attain the same resulting therapeutic nicotine level in the blood.

BRIEF DESCRIPTION OF THE DRAWINGS

FIG. 1 is a timeline illustrating a course of treatment according to the methods of the present invention shown at weekly intervals and beyond.

FIGS. 2 and 3 illustrate the frequency distribution of patch dose in mg nicotine/16-hour intervals computed by the dosing algorithm of the present invention for each of the active, cotinine replacement conditions of 50% (FIG. 2) and 100% (FIG. 3) replacement, respectively.

FIGS. 4 and 5 show the frequency distribution of percentage cotinine replacement actually achieved by the nicotine patch dose replacement conditions computed by the algorithms of the present invention.

FIG. 6 is a graph comparing the percentage of patients who have continued not to smoke based on cotinine replacement levels of 100%, 50%, and 0%.

FIG. 7 is a graph similar to FIG. 6 showing the percentage of patients who continued not smoking corrected to remove the underdosed subjects.

FIG. 8 is a graph showing an alternative data plot of patients who continued not smoking based on different cotinine replacement percentages.

FIG. 9 is a graph plotting the likelihood of continued abstinence of patients based on both their Fagerstrom number and the percentage cotinine replacement level achieved.

FIG. 10 is a plot similar to FIG. 9, shown with a different assumed dosage.

FIGS. 11 and 12 are plots of estimated probability of abstinence based on baseline serum cotinine at different replacement percentages.

FIG. 13 is a graph of data for a patient having a FTQ score of 7 and a cotinine replacement of 180%.

FIG. 14 is a plot of patient data based on equations 6 and 7 shown in the Experimental Section hereinbelow.

DESCRIPTION OF THE PREFERRED EMBODIMENT

Figure 1:
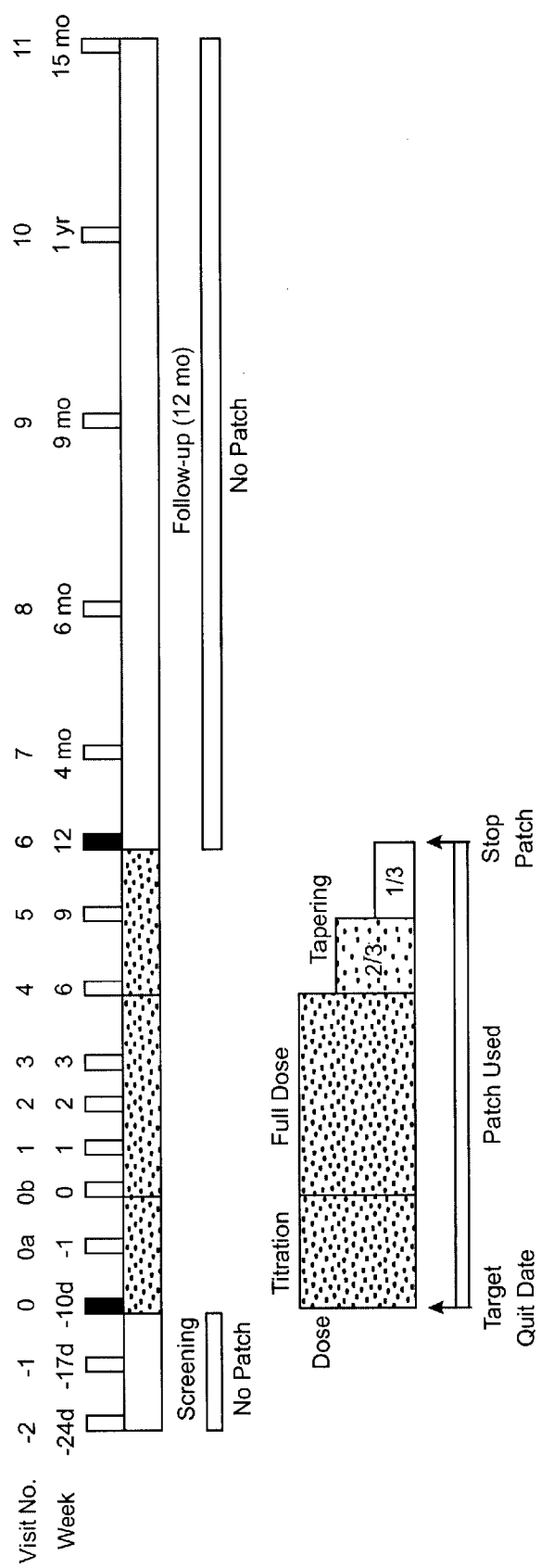
FIGS. 1–14 present data related to the examples provided in the Experimental section below.

The phrase "nicotine concentration" refers generally to blood and serum levels of nicotine present in a patient while smoking or during nicotine replacement therapy. As a practical matter, nicotine concentration measurements in blood and serum are very difficult, and it is preferred to measure stable nicotine metabolites in place of direct nicotine measurements. Particularly preferred is the measurement of cotinine which is a very stable nicotine metabolite having a half life of about 20 hours (in comparison to a half life of two hours for nicotine), which can be measured by known analytical techniques and which is considered an accepted marker for total nicotine intake. See, Jacob III et al. (1991) J. Chromatr. 222:61–70. Typically, nicotine replacement dosages will be chosen to provide nicotine blood concentrations (measured as cotinine) of at least about 40% of the pre-cessation value, usually being at least about 50%, and often being 100% (full replacement) or higher. Surprisingly, it has been found that it is often beneficial to increase the nicotine dosage sufficiently to raise serum nicotine metabolite levels to above 100% of the pre-cessation level, with values of 150% or more being found to provide improved nonsmoking compliance when compared to 100% replacement.

"Smoking" and "active smoking" refer to the smoking of tobacco products, particularly cigarettes. "Pre-cessation" refers to the period prior to beginning of cessation therapy where a patient is smoking tobacco products, where such smoking results in measurable levels of cotinine in the patient's blood. After smoking cessation therapy has commenced, it is expected that the patient will no longer smoke cigarettes or use any other tobacco products and that all nicotine and cotinine present in the blood will be derived from the nicotine replacement sources, as described in more detail hereinbelow.

"Patient characteristics" according to the present invention are selected to correlate and be predictive of the relationship between nicotine replacement dosage and blood concentrations of nicotine (measured as nicotine metabolite), and will usually be selected from the group consisting of a body mass factor, a cumulative smoking factor, a psychological dependence factor, age, and menopausal status (for women). While individual characteristics from this group have been found to be predictive in varying degrees of the relationship between nicotine replacement dosage and blood nicotine level, it should be appreciated that this list is not comprehensive and there will likely be other factors which could be identified in the future which could also be used as a basis for predicting such a relationship. Thus, this list is meant to be exemplary, and particularly useful in the practice of the present invention, but is not meant to be comprehensive or to exclude the use of other patient characteristics which might be employed in the methods of the present invention.

"Body mass factor" will generally be related to the patient's size and/or weight. Most simply, the body mass factor could be measured as weight, but will preferably be measured as a body mass index which is calculated as patient weight divided by height squared. Any conventional units can be employed, such as kilograms and meters, with variations in units being accounted for in the equation constants which are developed.

The "cumulative smoking factor" will account for the total amount of tobacco products smoked by the patient during the patient's life. Conveniently, the cumulative smoking factor will be the number of packs being smoked per day at a time immediately prior to the smoking cessation multiplied by the total number of years where the patient has smoked. Other equivalent cumulative smoking factors could also be devised.

The "psychological dependence factor" will generally be a subjective determination of psychological dependence on smoking and nicotine. Conveniently, such psychological dependence can be measured by a standardized test for nicotine dependence, such as the Fagerström Tolerance Questionnaire, as described in Fagerström (1978) Addic. Behav. 3:235–241. Briefly, the Fagerström Tolerance Questionnaire asks the patient to answer eight questions relating to smoking habits, resulting in a cumulative score in the range from zero to eleven, with higher scores being indicative of a greater dependence.

"Patient age" will generally be measured in years.

"Menopausal status" relates to whether a female patient is pre-menopausal or post-menopausal. Patients undergoing hormone replacement therapy (estrogen and progesterone) will be considered to be pre-menopausal. In pre-menopausal patients, the factor drops out of the equation described below. For post-menopausal women, the patient body mass factor is taken into account at least once. That is, in certain equations generated by the method of the present invention, body mass factor will be taken into account for all female patients. Those patients who are post-menopausal, the body mass factor will be taken into account a second time in predicting blood nicotine level as a function of nicotine dosage.

Using these patient characteristics, it will be possible to determine the relationship between nicotine dosage and blood nicotine levels (measured as a stable nicotine metabolite such as cotinine) in patients as a function of at least two of the patient characteristics just described. For male patients, the characteristics which have been found to have the strongest correlation with blood nicotine levels are body mass factor and the cumulative smoking factor. The third most important factor is psychological dependence, while age is the least important of the factors, although still relevant. For female patients, surprisingly, the order of importance of these factors is entirely different. The most important factors are psychological dependence and age. The third most important factor is menopausal status (where it determines whether a body mass factor is to be taken into account), while the fourth most important factor is the body mass factor (regardless of menopausal status). The cumulative smoking factor appears to be of little importance in predicting blood nicotine levels in women.

The particular formulas and relationships which are derived for predicting blood nicotine levels in patients based on nicotine dosage levels will also be strongly dependent on the nicotine source. It will be appreciated that different nicotine replacement sources will have significantly different pharmacokinetic characteristics which have a strong influence on the blood levels achieved. The present invention for the first time, however, recognizes that a variety of patient characteristics (in addition to the type and dosage of the nicotine replacement source) will be relevant in predicting blood nicotine levels (measured as a stable nicotine metabolite) in a patient for a given dosage. Moreover, by taking at least two of these characteristics into account, it will be possible to develop reliable pharmacokinetic models which allow prediction of the serum nicotine levels achieved with a given dosage for a particular nicotine replacement product. For example, equations can be developed for each of the transdermal patches which are presently on the market and any additional transdermal patches which may be developed in the future. Other models can be developed for other controlled nicotine replacement sources, such as chewing gums which provide for oral nicotine replacement.

In the Experimental section hereinbelow, particular equations are provided which relate the blood nicotine level (measured as cotinine metabolite) in men and women based on the application of a single Nicotrol™ (produced by Cygnus Therapeutic Systems, Redwood City, Calif., and supplied by Pharmacia AB, Helingborg, Sweden, and distributed in the United States by Mc Neil Consumer Products, Fort Washington, Penn.) nicotine patch. It will be appreciated that similar analysis techniques can be used for providing equations which allow prediction of blood nicotine levels when using other transdermal patches, as well as other nicotine replacement sources, and further that similar equations can be generated to predict blood nicotine levels for different dosages of nicotine from such nicotine patch and other sources.

The following examples are offered by way of illustration, not by way of limitation.

EXPERIMENTAL

MATERIALS AND METHODS

1. STUDY DESIGN

Subject Characteristics.

Subjects were smokers, aged 18 years or more, were eligible if they had smoked at least 10 cigarettes per day for a minimum of 3 years, were motivated to stop smoking completely, and were basically in good health. Exclusion criteria were severe or symptomatic cardiovascular disease, pregnancy or breast feeding, current regular use of psychotropic medications, current or past alcohol or other drug abuse, current use of smokeless tobacco, or chronic dermatological disorders such as psoriasis, urticaria, or chronic dermatitis.

Allocation to Treatment.

Subjects were sequentially and randomly assigned to receive one of three treatments based on a target percent cotinine replacement (% Cot Repl): 0% (placebo), 50%, or 100% cotinine replacement. In addition, subject enrollment was stratified by sex and nicotine dependency according to Table 1. Ninety-one subjects were assigned into the matrix shown in Table 1 with the "N" as shown.

TABLE 1

Assignment of Study Patients by Treatment Condition, Stratified by Sex and Nicotine Dependency*
(N = 91)

| | Target Serum Cotinine Replacement Level[†] from Nicotine Patch Treatment[‡] | | |
|---|---|---|---|
| Sex | 0% Replacement (N = 31) | 50% Replacement (N = 29) | 100% Replacement (N = 31) |
| Male | Hi Dep. = 7 Pts. | Hi Dep. = 9 Pts. | Hi Dep. = 9 Pts. |
| | Lo Dep. = 9 Pts. | Lo Dep. = 7 Pts. | Lo Dep. = 7 Pts. |
| Female | Hi Dep. = 8 Pts. | Hi Dep. = 8 Pts. | Hi Dep. = 8 Pts. |
| | Lo Dep. = 7 Pts. | Lo Dep. = 5 Pts. | Lo Dep. = 7 Pts. |

TABLE 1-continued

Assignment of Study Patients by Treatment Condition,
Stratified by Sex
and Nicotine Dependency*
(N = 91)

Target Serum Cotinine Replacement Level[†]
from Nicotine Patch Treatment[‡]

| Sex | 0% Replacement (N = 31) | 50% Replacement (N = 29) | 100% Replacement (N = 31) |
|---|---|---|---|

*As assessed by the Fagerström Tolerance Questionnaire (FTQ). FTQ range is 0 to 11 points. High Dependence is ≧ 7 points; Low Dependence is < 7 points
[†]% Cotinine Replacement = [Serum Cotinine (ng/ml) from Nicotine Patch Therapy ÷ Baseline Serum Cotinine (while smoking)] × 100
[‡]All patients were given three patches to wear each day. For those in the 0% replacement condition, all patches were 30 $cm^2$, placebo patches, containing 0 mg nicotine. For those in the 50% or 100% replacement conditions, the total nicotine patch dose, delivered by the three patches, could be from 5 mg to 45 mg nicotine/16 hours, whatever was necessary to meet the required value of the algorithm (SODA ™). If a patient needed only 5 mg nicotine/day, then he or she would have been given one, 10 $cm^2$, active patch (delivering 5 mg nicotine/16 hrs) together with two, 30 $cm^2$, placebo patches. On the other hand, if a patient needed the maximum dose provided by the study design, 45 mg nicotine/day, then he or she would have been given three, 30 $cm^2$, active patches, each delivering 15 mg nicotine/16 hrs.

Pharmacological Treatment.

Subjects were instructed to apply a number of new skin patches (assigned and dispensed in a double-blind manner as described below) each morning to a clean, non-hairy area of intact skin which had not been used as a patch application site within the last week, and to remove their assigned patches at bedtime. At each visit, subjects were supplied with a sufficient number of each of the assigned patches to cover the interval until the next visit. The placebo patches were identical to the active patches in appearance, packaging, and labeling, but contained no nicotine.

Full Treatment.

The study was designed to provide patients with six weeks of patch treatment at their randomly assigned target replacement level, with six additional weeks of structured tapering. Treatment consisted of daily use of the appropriate, double-blind combination of active and/or placebo skin patches.

Structured Tapering.

After using a sufficient number of nicotine patches each day to achieve their target cotinine replacement level for six full weeks, subjects were then provided with a three-week supply of the same three patches and with a template enabling them to easily and quickly cut one-third of each patch off, so that the total nicotine dose delivered was reduced by one-third. Throughout this tapering phase (weeks 6–12) all subjects continued to wear their same three nicotine patches each day, but with the size of each patch reduced by this template. At the second-to-last treatment visit (week 9) subjects were then given a three-week supply of their assigned patches and instructed to use the template to cut and remove two-thirds of each patch. Thus, they were applying three patches one-third the size, and therefore one-third the dose, of what they had been applying for the first six weeks of the program. At the end of these last three weeks of tapering (study week 12) no additional patches were provided.

2. DETERMINATION OF NICOTINE PATCH DOSE

Patch dose was computed by a group of research staff (the dosing management staff) separate from the clinical research staff. Communication between the dosing management staff and the clinical research staff regarding a given subject was carried out using each subject's unique medication identification number. This way, the double-blind was fully maintained. The clinical research staff knew and regularly saw each patient but was completely blind to the content of each of the three nicotine patches they dispensed to each subject at each visit. The dosing management staff knew precisely the content of each of the three patches that would be given to each-subject at each visit, but they never had any contact with any of the study subjects. The dosing management staff did not communicate information regarding nicotine patch content to the clinical research staff or to the patient.

The clinical research staff provided the dosing management staff with all of the information necessary to define the variables used in the dose determination algorithm (described below), except for the serum cotinine measurement which was measured by the dosing management staff and not transmitted back to the clinical research staff. Once the dosing management staff had employed the algorithm to compute the daily nicotine patch dose required to achieve the target percent cotinine replacement (% Cot Repl) level, they then packaged the appropriate combination of nicotine patches to reach that dose.

The Sachs Optimal Dosing Algorithm (SODA™).

The dosing algorithm is referred to hereinafter as the Sachs Optimal Dosing Algorithm (SODA™) and was initially developed from data taken from a 220-subject nicotine patch trial database. The primary outcome results from this trial's database have been reported elsewhere (Sachs et al. (1993) Arch. Int. Med. 153:1881–1890). The present data provide a confirmation and validation of the accuracy of the SODA™ in predicting serum cotinine level in a particular individual that will be attained by a given nicotine patch dose.

When developing the SODA™, it was found that there were major differences in constants and variables to predict cotinine blood levels while on nicotine patch therapy for men and for women. Consequently, separate prediction equations were developed for each sex. The equations used in the present study were as follows:

For men, venous serum cotinine level (ng/ml) achieved by the daily application of one patch delivering 15 mg/16 hr of nicotine is predicted by:

$$Cot_{R \times M} = 338.66864 - 9.34216\ BMI - 0.75199\ PkYrs + 0.40385\ Age + 0.08776\ Cot_{Smok} + 2.79601\ FTQ \quad (1)$$

$(r=0.7654, p=0.0064)$

Where:

$Cot_{R \times M}$=Venous serum cotinine (ng/ml) resulting in males from daily application of patch delivering 15 mg/16 hr of nicotine.

BMI=Body Mass Index=weight/(height)$^2$ in kg/m$^2$;

PkYrs=Pack Years=number of years smoked×number of cigarette packs smoked/day prior to cessation therapy;

FTQ=Fagerström Tolerance Questionnaire Score (0–11 scale: 0–6 corresponds to low dependence, 7–11 corresponds to high dependence);

Age=Age (in years); and $Cot_{Smok}$=venous serum cotinine (in ng/ml) prior to cessation therapy.

For women, venous serum cotinine level (ng/ml) achieved by the daily application of one patch delivering 15 mg/16 ml of nicotine is predicted by:

$$Cot_{R \times F} = 129.93686 + 3.93846\ BMI + 0.02047\ PkYrs - 2.25053\ Age + 0.31122\ Cot_{Smok} - 12.00131\ FTQ + 1.79433\ (MP)(BMI) \quad (2)$$

$(r=0.6944, p=0.0071)$

Where:

MP=Menopausal status=1 for pre-menopausal patients and 0 for post-menopausal patients.

(All other variables are as defined for equation (1))

These were the equations used by the dosing management staff to compute nicotine patch dose before the clinical research staff gave each patient his or her initial blinded study drug supply at Visit 0, just before Target Quit Date.

Three days after Target Quit Date, i.e., three days after stopping smoking and beginning application of their daily nicotine patch dose, subjects returned for Visit 0a, at which time venous blood level was obtained to measure nicotine and cotinine levels attained by that patch dose. Based on the actual cotinine measured at Visit 0a against the predicted cotinine from the SODA™ at Visit 0, the dosing management staff recomputed the nicotine patch dose to try to better achieve the actual target replacement condition (50% cotinine replacement or 100% cotinine replacement) for each individual patient. One week after Visit 0a, each subject returned for Visit 0b to receive the revised patch dosage. Subjects returned one week later (Visit 1) and blood was obtained for measurement of serum nicotine and cotinine levels. Nicotine patch dose, however, was not changed after Visit 0b.

Each patient came in for visits as shown in FIG. 1, i.e., at one week, two weeks, three weeks, and six weeks after Visit 0b. At the six-week visit (Visit 4), each patient was given the sizing template and instructed how to cut each of their three patches for the next three weeks (weeks 6–9) to reduce the total nicotine dose by one-third. At Visit 5 (week 9) each patient was individually instructed how to use the sizing template to reduce the original nicotine dose used during the first six weeks by two thirds. This reduced-dose was equal to one-third of the dose during the first six weeks and was used for the last three weeks of tapering (weeks 9–12).

Behavioral Treatment.

Throughout this study, patients were provided treatment and counseling described in Sachs et al. (1993), supra. In brief, at Screening Visit -2 (FIG. 1), each patient completed a detailed medical history (Health Record Questionnaire®, Pulmonary Diagnostic & Rehabilitation Medical Group Inc., Palo Alto, Calif.), had blood drawn for routine chemistry studies, and had posteroanterior and lateral chest roentgenograms and a 12-lead electrocardiogram taken. No group counseling sessions were used, nor were any special psychological or behavioral modification techniques employed. Only skills that any physician and professional staff in the medical office could readily provide were used.

The physician, during the 45 to 60 minute physical examination, linked any relevant findings from the medical history, laboratory examination, and physical examination with the specific benefits that each individual patient could reasonably expect to gain by stopping smoking. If the patient met all inclusion-exclusion criteria, then the physician gave the patient a copy of the self-help video tape *Stop for Good: A Video House Call* [Video] (Feeling Fine Programs, Inc. Los Angeles, Calif. 1991). The physician advised the patient to use this video book between this visit and the next one, Visit 0, which was scheduled to be the day before the patient's individual Target Quit Date, to develop an individual Action Plan for coping with situations that could trigger an urge for cigarettes.

At each of the subsequent visits, project personnel completed data collection forms, monitored patch compliance, assessed adverse events, collected all used and unused patches, drew venous blood for subsequent nicotine and cotinine level determination, measured vital signs, including weight, and determined exhaled air carbon monoxide level to verify nonsmoking status objectively. Other than the time necessary to complete the above activities, time that project personnel spent with an individual patient was kept to a minimum, approximately 10–15 minutes. During that time, at each visit from Target Quit Date through six months (FIG. 1), each patient received brief, individualized, common-sense, smoking cessation advice, from a medical perspective, from one of the project staff, on an as-needed basis.

Concurrent Medications and Therapy.

Subjects were allowed to take whatever other medications were needed to manage intercurrent illness as prescribed by project physicians or the patient's own physician. Meticulous records of any concomitant medications were carefully maintained. Subjects were not, at any time, allowed to use other anti-smoking medications (proved or potential), such as nicotine polacrilex (NicoretteQ), clonidine, anxiolytics, or anti-depressants. Similarly, subjects were not allowed to avail themselves of any other smoking cessation treatment, such as workplace group support programs or self-help manuals, other than what was provided to them during the course of this study.

3. OUTCOME MEASUREMENTS

Efficacy.

Patients were instructed to keep a daily diary record of any cigarettes smoked. Smoking abstinence was defined as (1) patient self-report of no smoking from Target Quit Date (in the case of the first visit following Target Quit Date) or from the previous visit (for all visits after the visit after Target Quit Date), with no deviations of any kind allowed (if the subject reported even one puff from a cigarette in the daily diary, then that patient was classified as a treatment failure) and (2) an exhaled air carbon monoxide level of nine parts per million or less at each visit. Subjects who used any other smoking cessation aids (behavioral or pharmacological), did not return for their follow-up visits, or were unavailable for follow-up were classified as smokers.

4. ANALYTIC METHODS

Demographic and smoking history variables were compared across treatment conditions to assess baseline comparability using the ANOVA. The primary efficacy measurement was time to relapse. This was calculated beginning at the end of the second week after Target Quit Date. Time to relapse, or survival time, for each patient was then calculated as the number of days until the patient first smoked, withdrew, or was dropped from the study, whichever occurred first. The generalized log-rank statistics and Wilcoxon statistics (Kaplan and Meir (1958) JASA 53:457–481) were used to determine significance at the end of the survival curve (life-table analysis). Additionally, at weeks 2, 3, 6, 9, 12, 16, and 26, trend comparison of cessation rates across dosing conditions were made using the two-tailed Mann-Whitney Two-Sample Rank Test.

RESULTS

1. SUBJECT CHARACTERISTICS

All Subjects.

Of 91 subjects randomized to the three cotinine replacement conditions, 43 were women and 48 were men. Their baseline characteristics are given in Table 2. There were no significant differences between active and placebo treatment group subjects.

TABLE 2

Baseline and Demographic Information*
All Patients (N = 91)

| | % Cotinine Replacement Condition | | |
|---|---|---|---|
| | 0% (Placebo) (N = 31) | 50% (N = 29) | 100% (N = 31) |
| Age (in years) | 46.4 ± 10.7 (21.3–65) | 43.7 ± 8.5 (27–58) | 46.7 ± 11 (25.2–64.6) |
| Sex, M/F (in %) | 51.6%/48.4% | 55.2%/44.8% | 51.6%/48.4% |
| Weight (in kg) | 76.7 ± 14.4 (45–102) | 79.9 ± 17.5 (54–124) | 75.1 ± 18.1 (44–109) |
| Nicotine Dependence[†] | 6.2 ± 1.8 (2–9) | 6.7 ± 2.2 (2–11) | 6.7 ± 1.7 (3–10) |
| # Cigarettes Smoked Per Day | 25.8 ± 13.2 (10–60) | 24.8 ± 11.2 (10–50) | 25.1 ± 10.0 (10–44) |
| # Years Smoked | 25.7 ± 12.7 (4–55) | 24.8 ± 8.8 (10–41) | 29.3 ± 11.1 (8–46) |
| Baseline Exhaled Air Carbon Monoxide (in ppm)[‡] | 26.7 ± 9.1 (15–52) | 31.6 ± 12.5 (15–73) | 28.5 ± 9.3 (15–50) |
| Baseline Serum Nicotine (in ng/ml)[‡] | 24.1 ± 7.7 (11.7–39.4) | 24.8 ± 8.9 (9.6–37.9) | 23.6 ± 6.9 (12.5–36.8) |
| Baseline Serum Cotinine (in ng/ml)[‡] | 283.3 ± 119.4 (38.8–512.5) | 267.6 ± 94.2 (84.6–422.0) | 267 ± 109.4 (119.5–576.0) |
| Age Started Smoking Cigarettes (in years) | 18.8 ± 4.4 (12–33) | 16.6 ± 3.1 (10–23) | 16.4 ± 2.2 (11–21) |
| # Previous Quit Attempts | 2.1 ± 1.4 (0–5) | 3.1 ± 3.0 (0–12) | 3.9 ± 4.2 (0–18) |

*There were no significant differences by treatment condition. Except as noted, values are mean ± SD (range).
[†]Measured by the Fagerstrom Tolerance Questionnaire (FTQ). Score range: 0–11. Low nicotine dependence $\leq$ 6. High nicotine dependence $\geq$ 7.
[‡]Baseline levels measured at the first and second screening visits, Study Visits −2 and −1, two weeks and one week before Target Quit Date, while patients were still smoking cigarettes at their baseline rate. Data for each patient were averaged for the two visits.

Baseline and Demographic Information For Sub-groups.

Later in this Results section, treatment results are presented for the two sub-groups: "All Randomized Patients Who Could Be Adequately Dosed with three Patches Delivering up to 45 mg Nicotine/16 Hours (N=81)" and "All Patients by % Cotinine Replacement Actually Attained (N=82)". Their baseline and demographic data are presented in Tables 2A and 2B. Although there were some statistically significant differences between treatment conditions, those appear to be relatively minor, and were considered unlikely to have had an impact on the results reported below.

TABLE 2A

Baseline and Demographic Information*
- All Randomized Patients Who Could Be Adequately Dosed With 3 Patches Delivering Up To 45 mg Nicotine/16 Hours -
(N = 81)

| | % Cotinine Replacement Condition | | |
|---|---|---|---|
| | 0% (Placebo) (N = 31) | 50% (N = 27) | 100% (N = 23) |
| Age (in years) | 46.4 ± 10.7 (21.3–65) | 43.1 ± 8.3 (27–58) | 45.8 ± 11.9 (25.2–64.6) |
| Sex, M/F (in %) | 52%/48% | 56%/44% | 35%/65% |
| Weight (in kg) | 76.7 ± 14.4 (45–102) | 78.2 ± 15.5 (54–124) | 69.5 ± 15.2 (44–100) |
| Nicotine Dependence[†] | 6.2 ± 1.8 (2–9) | 6.5 ± 2.1 (2–11) | 6.4 ± 1.6 (3–10) |
| # Cigarettes Smoked Per Day | 25.8 ± 13.2 (10–60) | 24.7 ± 11.6 (10–50) | 21.9 ± 8.9 (10–44) |
| # Years Smoked | 25.8 ± 12.7 (4–55) | 24.0 ± 8.5 (10–41) | 28.7 ± 12.3 (8–46) |
| Baseline Exhaled Air Carbon Monoxide (in ppm)[‡] | 26.7 ± 9.1 (15–52) | 31.9 ± 12.9 (15–73) | 27.0 ± 8.9 (15–45) |
| Baseline Serum Nicotine (in ng/ml)[‡] | 24.2 ± 7.7 (11.7–39.4) | 24.9 ± 9.1 (9.6–37.9) | 22.0 ± 5.7 (12.5–31.0) |
| Baseline Serum Cotinine (in ng/ml)[‡] | 283.3 ± 119.4 (38.8–512.5) | 272.4 ± 95.9 (84.6–422.0) | 231.7 ± 79.8 (119.5–417.0) |
| Age Started Smoking Cigarettes (in years) | 18.8 ± 4.4 (12–33) | 16.6 ± 3.2§ (10–23) | 16.4 ± 2.4§ (11–21) |
| # Previous Quit Attempts | 2.1 ± 1.4 (0–5) | 3.1 ± 3.1 (0–12) | 4.0 ± 3.5 (0–13) |

*There were no significant differences between treatment conditions, except as specified. Except as noted, values are mean ± SD (range).
[†]Measured by the Fagerstrom Tolerance Questionnaire (FTQ). Score range: 0–11. Low nicotine dependence $\leq$ 6. High nicotine dependence $\geq$ 7.
[‡]Baseline levels measured at the first and second screening visits, Study Visits −2 and −1, two weeks and one week before Target Quit Date, while patients were still smoking cigarettes at their baseline rate. Data for each patient were averaged for the two visits.
§$p < 0.05$, compared to 0% (placebo) condition, only.

TABLE 2B

Baseline and Demographic Information*
- All Patients by % Cotinine Replacement Actually Attained -
(N = 82)

| | % Cotinine Replacement Condition | | | |
|---|---|---|---|---|
| | 0% (Placebo) (N = 24) | >0%–<50% (N = 23) | $\geq$50%–<100% (N = 24) | $\geq$100% (N = 11) |
| Age (in years) | 46.0 ± 11.6 (21.3–65) | 42.3 ± 8.8§ (27–58) | 44.5 ± 9.3§ (25.2–60.2) | 53.8 ± 9.4 (38.3–64.6) |

TABLE 2B-continued

Baseline and Demographic Information*
- All Patients by % Cotinine Replacement Actually Attained -
(N = 82)

| | % Cotinine Replacement Condition | | | |
|---|---|---|---|---|
| | 0% (Placebo) (N = 24) | >0%–<50% (N = 23) | ≧50%–<100% (N = 24) | ≧100% (N = 11) |
| Sex, M/F (in %) | 58%/42% | 52%/48% | 46%/54% | 64%/36% |
| Weight (in kg) | 77.1 ± 12.6 (46–96) | 77.1 ± 16.0 (54–124) | 75.7 ± 15.6 (56–105) | 79.8 ± 26.2 (44–123) |
| Nicotine Dependence[†] | 6.0 ± 1.8 (2–9) | 6.3 ± 2.1 (2–11) | 7.0 ± 1.7 (3–10) | 6.5 ± 1.8 (3–9) |
| # Cigarettes Smoked Per Day | 25.0 ± 13.3 (10–60) | 24.1 ± 10.6 (10–50) | 25.9 ± 11.5 (10–50) | 24.2 ± 9.1 (10–40) |
| # Years Smoked | 24.4 ± 13.3§ (4–55) | 23.5 ± 8.3§ (10–41) | 26.9 ± 10.9§ (8–46) | 36.7 ± 8.3 (23–45) |
| Baseline Exhaled Air Carbon Monoxide (in ppm)[‡] | 26.3 ± 8.2 (15–41) | 30.9 ± 13.7 (15–73) | 30.0 ± 9.4 (15–50) | 25.2 ± 6.7 (18–39) |
| Baseline Serum Nicotine (in ng/ml)[‡] | 23.3 ± 7.3 (11.7–38.4) | 23.4 ± 9.8 (9.6–37.9) | 25.0 ± 6.2 (14–36) | 23.2 ± 6.9 (13.5–36.8) |
| Baseline Serum Cotinine (in ng/ml)[‡] | 265.9 ± 123.3 (38.8–512.5) | 262.5 ± 102.6 (84.6–422.0) | 288.0 ± 118.8 (119.5–576.0) | 230.9 ± 49.5 (180.5–354.5) |
| Age Started Smoking Cigarettes (in years) | 19.3 ± 4.5 (12–33) | 16.8 ± 3.0¶ (10–23) | 16.0 ± 2.8¶ (10–21) | 16.5 ± 1.8¶ (14–20) |
| # Previous Quit Attempts | 2.1 ± 1.3 (0–5) | 3.3 ± 2.9 (0–12) | 3.5 ± 4.4 (0–18) | 4.1 ± 4.1 (0–13) |

*There were no significant differences between treatment conditions, except as specified. Except as noted, values are mean ± SD (range).
[†]Measured by the Fagerstrom Tolerance Questionnaire (FTQ). Score range: 0–11. Low nicotine dependence ≦ 6. High nicotine dependence ≧ 7.
[‡]Baseline levels measured at the first and second screening visits, Study Visits -2 and -1, two weeks and one week before Target Quit Date, while patients were still smoking cigarettes at their baseline rate. Data for each patient were averaged for the two visits.
§$p < 0.05$, compared to ≧ 100% condition, only.
¶$p < 0.05$ compared to 0% (placebo) condition, only.

2. ACCURACY OF THE SACHS OPTIMUM DOSING ALGORITHM (SODA™) IN PREDICTING SERUM COTININE LEVEL FROM TREATMENT.

All Randomized Patients (N=91).

Figure 2:
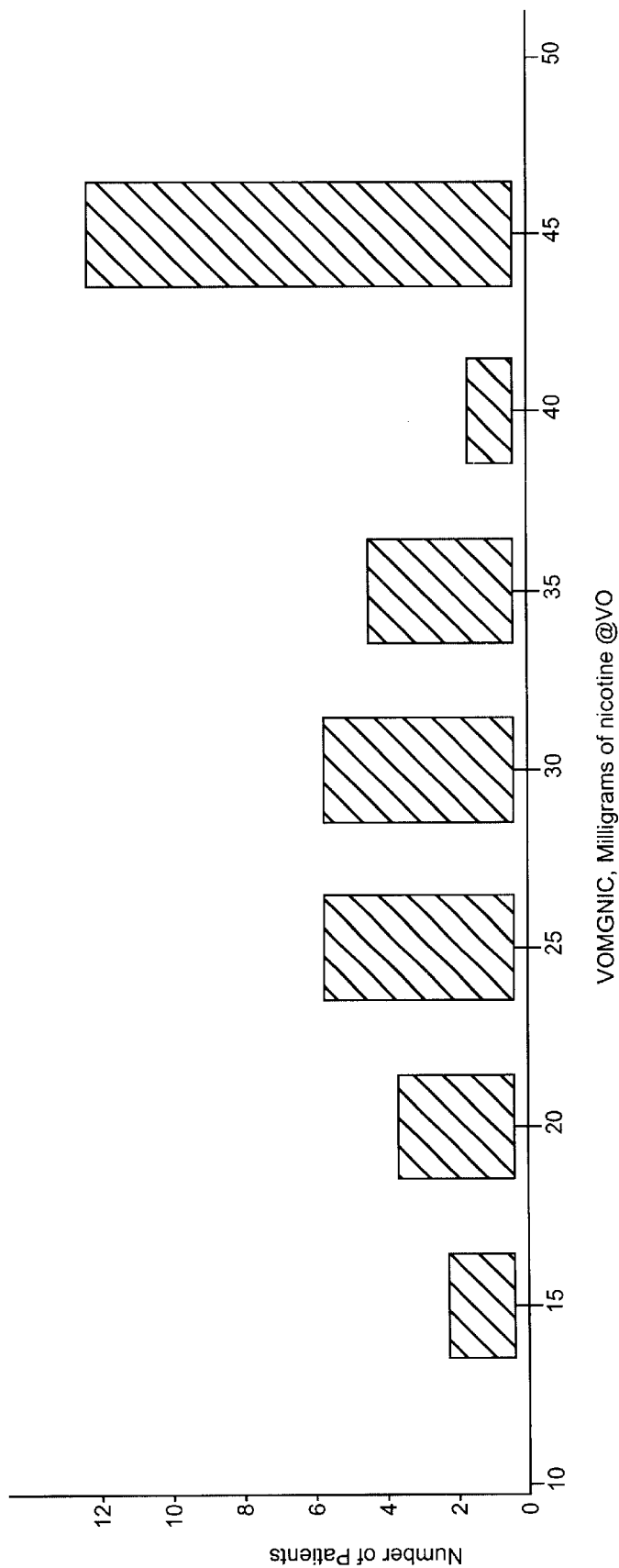
Figure 3:
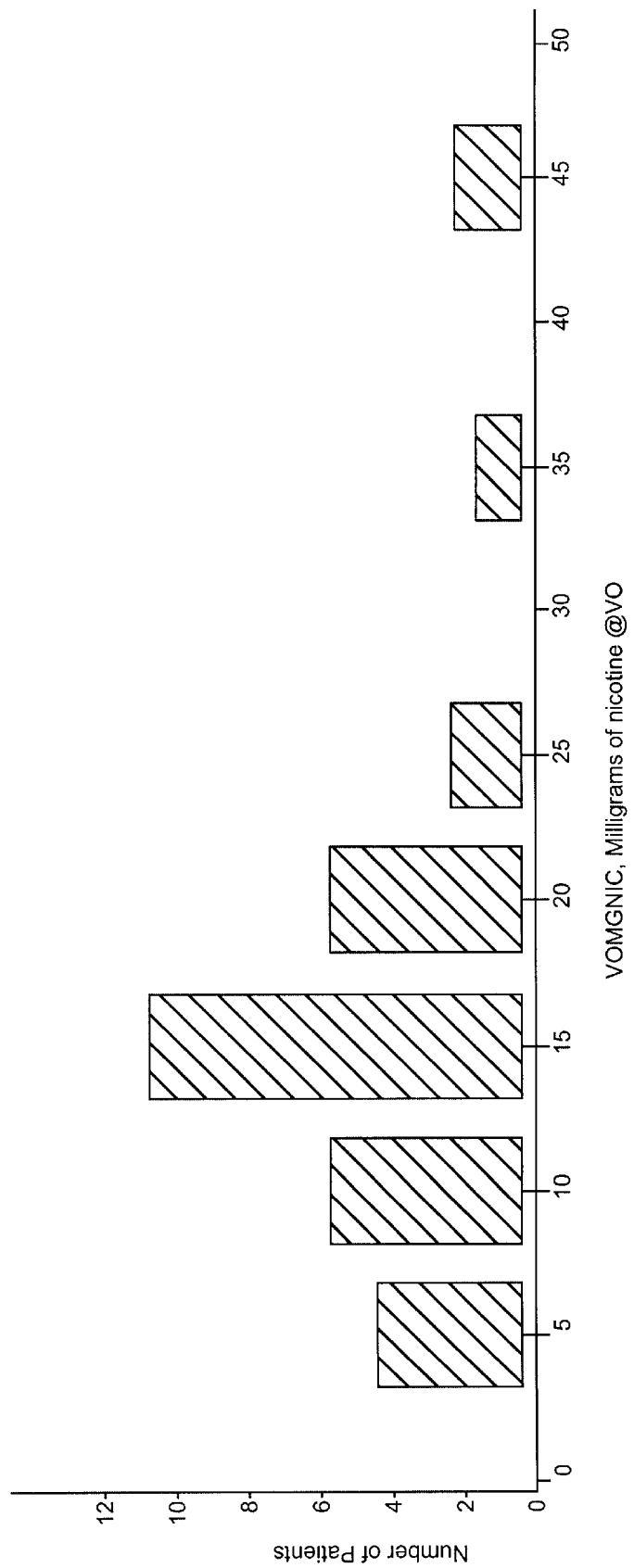

The baseline serum cotinine levels (ng/ml), from Screening Visits -2 and -1 for each patient were used to compute the nicotine patch dose to be prescribed at Visit 0, as shown in Table 3. FIGS. 2 and 3 show the frequency distribution of patch dose in mg nicotine/16-hours computed by the SODA™ for each of the active, cotinine replacement conditions, 50% and 100% replacement, respectively.

TABLE 3

SODA ™ Computed Nicotine Patch Dose to be Prescribed at Visit 0
to Attain Indicated Target % Cotinine Replacement Condition.
All Randomized Patients (Active Conditions Only).

| | % Cotinine Replacement Condition | |
|---|---|---|
| | 50% (N = 29) | 100% (N = 31) |
| Mean Nicotine Patch Dose (mg nicotine/16 hours) | 17.1 ± 10.2 mg* (5–45 mg) | 33.5 ± 10.3 mg[†] 15–45 mg) |
| Median Nicotine Patch Dose (mg nicotine/16 hours) | 15 mg | 35 mg |
| Mode Nicotine Patch Dose (mg nicotine/16 hours) | 15 mg | 45 mg |

TABLE 3-continued

SODA ™ Computed Nicotine Patch Dose to be Prescribed at Visit 0
to Attain Indicated Target % Cotinine Replacement Condition.
All Randomized Patients (Active Conditions Only).

| | % Cotinine Replacement Condition | |
|---|---|---|
| | 50% (N = 29) | 100% (N = 31) |

*Values are mean ± SD (range).
[†]$P < 0.0001$ compared to 50% replacement condition.

When patients returned three days later (Visit 0a), after not having smoked during that interval, blood was drawn to enable recomputation of the nicotine patch dose that would then be prescribed 1 week later, 10 days after Visit 0 (Visit 0b). Those doses, adjusting for the levels achieved by the SODA™s first iteration, are shown on Table 3A.

TABLE 3A

SODA ™ Computed Nicotine Patch Dose to be Prescribed at Visit 0b, to Attain Indicated Target % Cotinine Replacement Condition.
All Randomized Patients (Active Conditions Only).

| | % Cotinine Replacement Condition | |
|---|---|---|
| | 50% (N = 29) | 100% (N = 31) |
| Mean Nicotine Patch Dose (mg nicotine/16 hours) | 20.9 ± 10.9 mg* (5–45 mg) | 36.1 ± 9.1 mg† (15–45 mg) |
| Median Nicotine Patch Dose (mg nicotine/16 hours) | 15 mg | 40 mg |
| Mode Nicotine Patch Dose (mg nicotine/16 hours) | 15 mg | 45 mg |

*Values are mean ± SD (range).
†$P < 0.0001$ compared to 50% replacement condition These data clearly show that the SODA™ prescribes substantially different nicotine patch doses based on the desired or targeted cotinine replacement level which the nicotine patch is intended to achieve.

Figure 4:
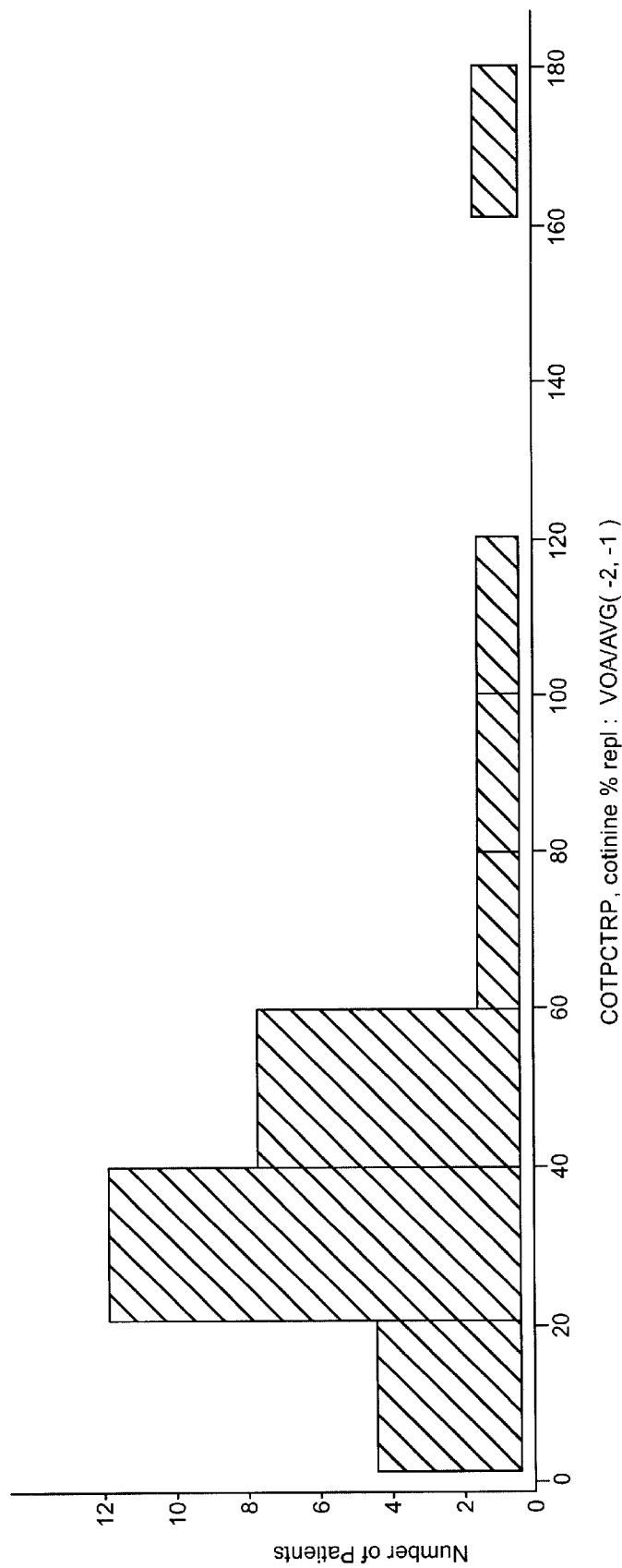
Figure 5:
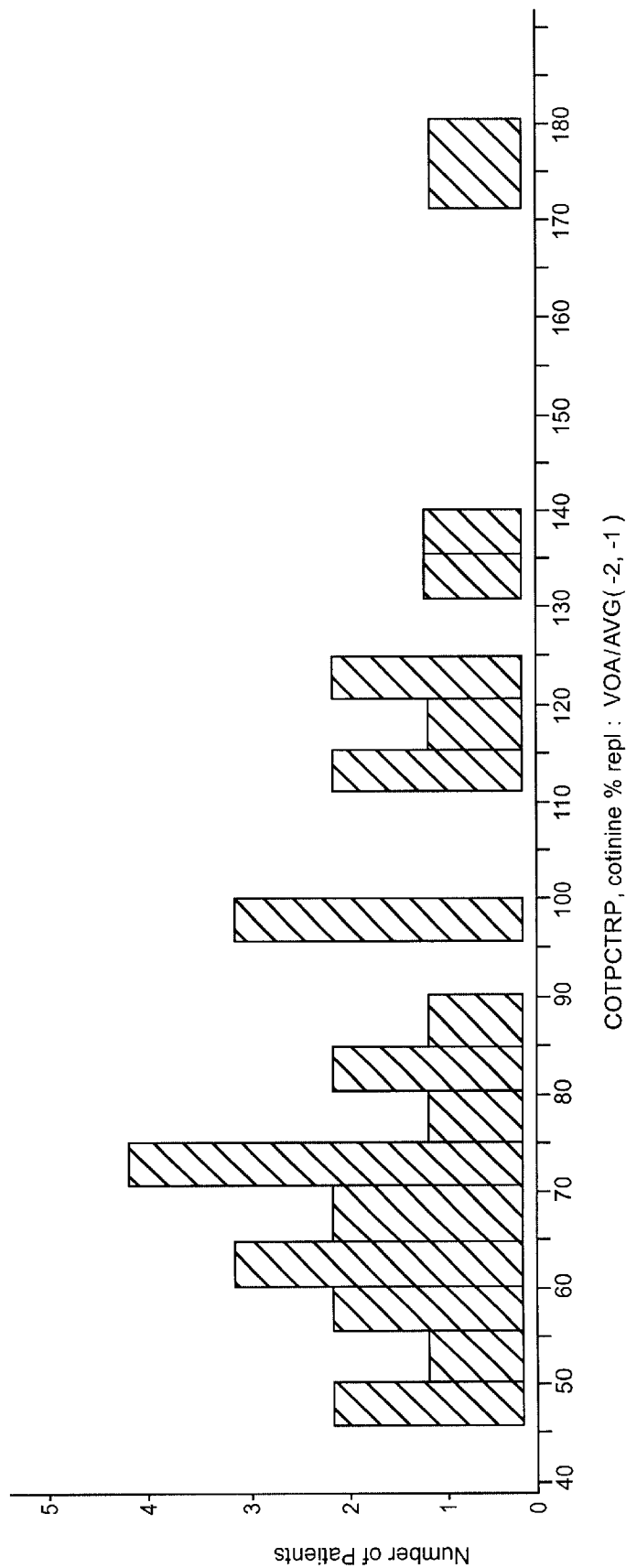

Table 4 shows the actual cotinine replacement percentages achieved by the individualized nicotine patch dose, measured at Visit 0a, as computed by the SODA™, for each of the two active replacement conditions. FIGS. 4 and 5 show the frequency distribution of percentage cotinine replacement actually achieved by the nicotine patch dose computed by the SODA™ for each of the active, cotinine replacement conditions. These data clearly show that on the first dosing iteration, as measured at Visit 0a, the SODA™ was within 5% and 10% of the target cotinine replacement levels, respectively. Thus, the SODA™ predicts required nicotine patch dose accurately. Note that for both target conditions, the SODA™ slightly underestimated the nicotine patch dose actually necessary to achieve the target replacement level. The difference between the mean cotinine replacement actually achieved for the patients assigned to the 100% condition vs. those assigned to the 50% condition was highly statistically significantly different (P-value<0.0001), while the difference between the mean cotinine replacement percentage actually achieved vs. the target was not significantly different (P=0.3843 for the 50% replacement condition and P=0.1273 for the 100% condition).

TABLE 4

Actual % Cotinine Replacement Achieved by the Nicotine Patch Dose Prescribed at Visit 0 (Table 3) Measured at Visit 0a. All Randomized Patients (Active Conditions, Only)

| | Target % Cotinine Replacement | |
|---|---|---|
| | 50% (N = 29) | 100% (N = 31) |
| Mean Cotinine Replacement Attained* | 44.5 ± 32.2%¹,‡ (15.5–169.2%) | 90.0 ± 35.0%§,♦ (46.7–177.4%) |
| Median Cotinine Replacement Attained | 35.3% | 35.3% |

*% Cotinine Replacement = [Serum Cotinine Level (in ng/ml) from Nicotine Patch ÷ Serum Cotinine Level (in ng/ml) from Cigarettes (while smoking) ] × 100.

TABLE 4-continued

Actual % Cotinine Replacement Achieved by the Nicotine Patch Dose Prescribed at Visit 0 (Table 3) Measured at Visit 0a. All Randomized Patients (Active Conditions, Only)

| | Target % Cotinine Replacement | |
|---|---|---|
| | 50% (N = 29) | 100% (N = 31) |

¹Values are means ± SD (range).
‡P = 0.3843 for mean % Cotinine Replacement compared to the target (50%, in this case).
§P < 0.0001 compared to 50% Replacement Condition.
♦P = 0.1273 for mean % Cotinine Replacement compared to the target (100%, in this case).

All Randomized Patients Who Could Be Adequately Dosed with Three Patches Delivering up to 45 mg Nicotine/16 Hours (N=81).

After completing this study and beginning data analysis, it became apparent that three patches, delivering 45 mg nicotine/16 hours, was not a high enough dose for all of the subjects in this trial to enable them to achieve their target cotinine replacement level. Consequently, a post-hoc analysis was performed eliminating those patients who could not have achieved their target cotinine replacement level with the maximum number of patches allowed: three patches delivering 45 mg nicotine/16 hours. Ten patients met this definition. Elimination of those ten individual left a sample size N of 81. (When the upper nicotine dosing bound of 45 mg was removed, the eight subjects randomized to the 100% replacement condition would have needed a nicotine patch dose between 50 and 90 mg nicotine/16 hours.) Table 5 shows the nicotine patch doses, prescribed and actually issued at Visit 0, for the 50 nicotine-treated subjects who could be adequately dosed given the three patch boundary-limit in this study design. Table 5A shows the nicotine patch doses prescribed and actually issued at Visit 0b, for the same 50 patients, after adjusting for the actual cotinine replacement levels achieved by the SODA™s first iteration. Table 6 shows the actual % Cot Repl achieved by the individualized nicotine patch dose, as computed by the SODA™, for all subjects who could reach their target cotinine replacement level with three nicotine patches or less.

TABLE 5

SODA ™ Computed Nicotine Patch Dose to be Prescribed at Visit 0, to Attain Indicated Target % Cotinine Replacement Condition. All Randomized Patients Who Could Be Adequately Dosed with Three Patches Delivering Up To 45 mg Nicotine/16 Hours (Active Conditions Only).

| | Cotinine Replacement Condition | |
|---|---|---|
| | 50% (N = 27) | 100% (N = 23) |
| Mean Nicotine Patch Dose (mg nicotine/16 hours) | 14.0 ± 6.9 mg* (5–35 mg) | 29.6 ± 8.9 mg¹ (15–45 mg) |
| Median Nicotine Patch Dose (mg nicotine/16 hours) | 15 mg | 30 mg |
| Mode Nicotine Patch Dose (mg nicotine/16 hours) | 15 mg | 15 mg |

*Values are means ± SD (range)
¹$P < 0.0001$ compared to 50% replacement condition.

TABLE 5A

SODA ™ Computed Nicotine Patch Dose to be Prescribed at Visit 0b, to Attain Indicated Target % Cotinine Replacement Condition.
-All Randomized Patients Who Could Be Adequately Dosed With 3 Patches Delivering Up To 45 mg Nicotine/16 Hours (Active Conditions Only)-

| | Cotinine Replacement Condition | |
|---|---|---|
| | 50% (N = 27) | 100% (N = 23) |
| Mean Nicotine Patch Dose (mg nicotine/16 hours) | 21.1 ± 11.2 mg* (5–45 mg) | 33.9 ± 9.4 mg[1] (15–45 mg) |
| Median Nicotine Patch Dose (mg nicotine/16 hours) | 15 mg | 35 mg |
| Mode Nicotine Patch Dose (mg nicotine/16 hours) | 15 mg | 45 mg |

*Values are means ± SD (range)
[1]P < 0.0001 compared to 50% replacement condition.

TABLE 6

Actual % Cotinine Replacement Achieved by the Nicotine Patch Dose Prescribed at Visit 0 (Table 5), Measured at Visit 0a. All Randomized Patients Who Could Be Adequately Dosed With Three Patches Delivering Up To 45 mg Nicotine/16 Hours (Active Conditions Only)

| | Target % Cotinine Replacement | |
|---|---|---|
| | 50% (N = 27) | 100% (N = 23) |
| Mean Cotinine Replacement Attained* | 37.3 ± 17.1%[1,‡] (15.5–85.6%) | 89.3 ± 37.4%[§,♦] (46.7–177.4%) |
| Median Cotinine Replacement Attained | 34.0% | 79.1% |

*% Cotinine Replacement [Serum Cotinine Level (in ng/ml) from Nicotine Patch ÷ Serum Cotinine Level (in ng/ml) from Cigarettes (while smoking) × 100.]
[1]Values are mean ± SD (range).
‡P = 0.0011 for mean % Cotinine Replacement compared to the target (50%, in this case).
§P < 0.0001 compared to 50% Replacement Condition.
♦P = 0.1858 for mean % Cotinine Replacement compared to the target (100%, in this case).

As with all of the randomized patients (N=91), the difference between the mean % Cot Repl actually achieved for the patients assigned to the 100% condition and those assigned to the 50% condition was highly statistically significantly different (P<0.0001). The difference between the mean cotinine replacement percentage actually achieved vs. the target replacement percentage continued not to be significantly different for the 100% cotinine replacement condition (P=0.1858). Interestingly, when the subjects assigned to the 50% nicotine replacement condition were so adjusted, the percentage cotinine replacement actually achieved fell further (44.5% to 37.3%) and was significantly below the 50% target (P<0.002), see Table 6.

2. TREATMENT EFFECTIVENESS PRODUCED BY INDIVIDUALIZING NICOTINE PATCH DOSE TO ACHIEVE A TARGET % COTININE REPLACEMENT LEVEL.

Survival Analysis.

All randomized patients (N=91). Throughout the six-week treatment period plus the six-week tapering period, the higher the replacement condition, the better the sustained smoking cessation rate: 100% Cot Repl consistently had better results than the 50% Cot Repl condition, which, in turn, produced consistently better results than the placebo condition (0% Cot Repl) (Wilcoxon P<0.02), see FIG. 6.

Figure 7:
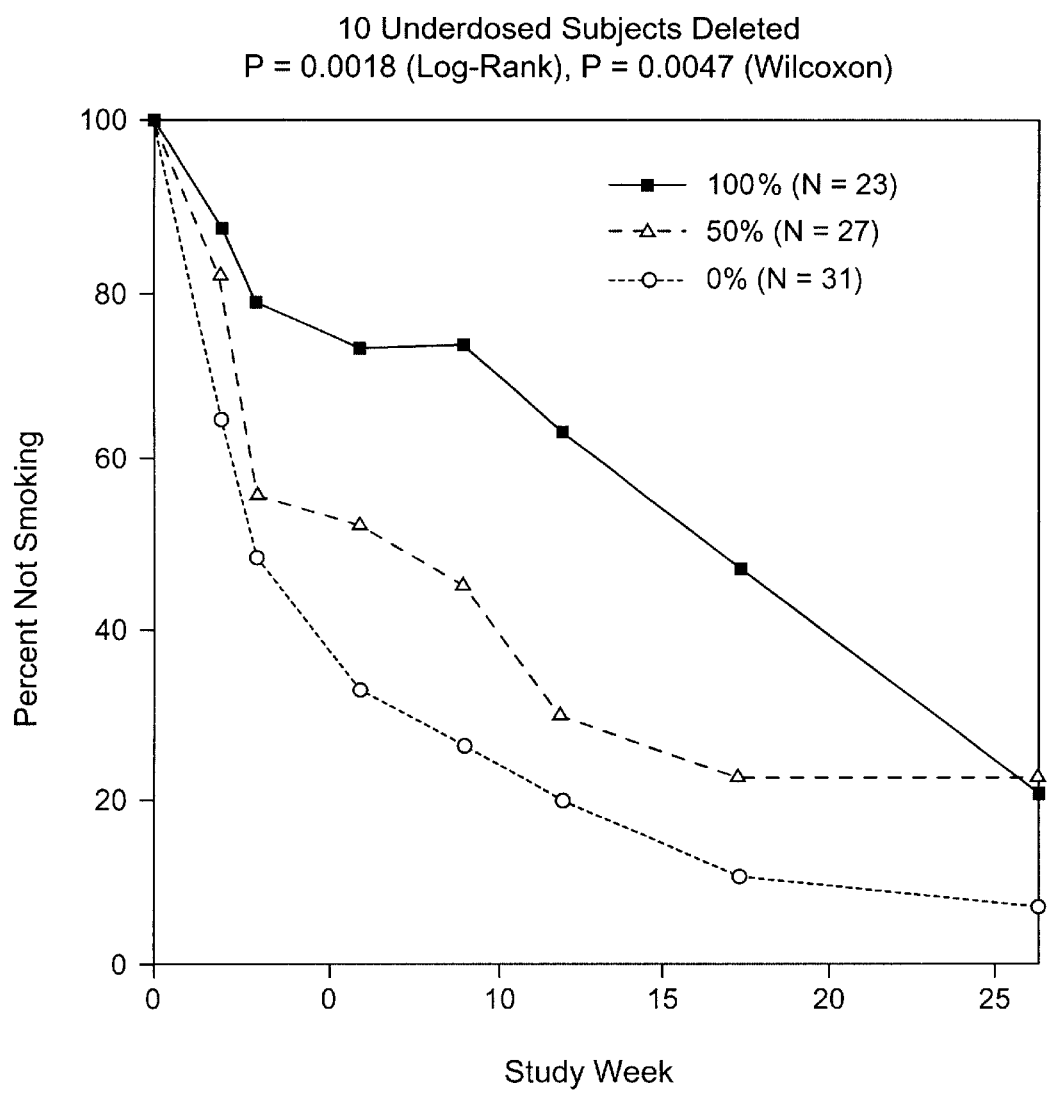

All randomized patients who could be adequately dosed with three patches delivering up to 45 mg nicotine/16 hours (N=81). FIG. 7 shows that when the analysis included only the 81 patients who could achieve their target cotinine replacement level with a nicotine patch dose up to 45 mg nicotine/16 hours, then the benefits of individualizing nicotine patch dose to achieve 100% cotinine replacement were even greater. Both the Wilcoxon and log-rank P-values were significant at P<0.005 or better. Twelve-week continuous nonsmoking rates were boosted by more than 50% for those patients who had been randomized to achieve 100% cotinine replacement, compared to those who had been randomized to achieve 50% cotinine replacement: 63% nonsmoking vs. 30% nonsmoking (P<0.007), see Table 8.

All patients by percent cotinine replacement actually attained (N=82). Post-hoc survival curves were also generated based on the percent cotinine level actually attained, irrespective of the original condition that subjects had been randomized to. To accomplish this, only those patients who had not smoked any cigarettes in the three days after their Target Quit Date until their Visit 0a (See FIG. 1) were included. There were 82 patients who said they had not smoked, had daily diaries that confirmed that, and had an exhaled air carbon monoxide level of 9 parts per million or less at Visit 0a. With these 82 subjects, the % Cot Repl was computed by the following equation:

$$\% \text{ Cot Repl} = [\text{Serum Cotinine (ng/ml) from nicotine patch dose at Visit 0a} \div \text{Serum Cotinine (ng/ml) from cigarette smoking at baseline}] \times 100. \quad (3)$$

Figure 8:
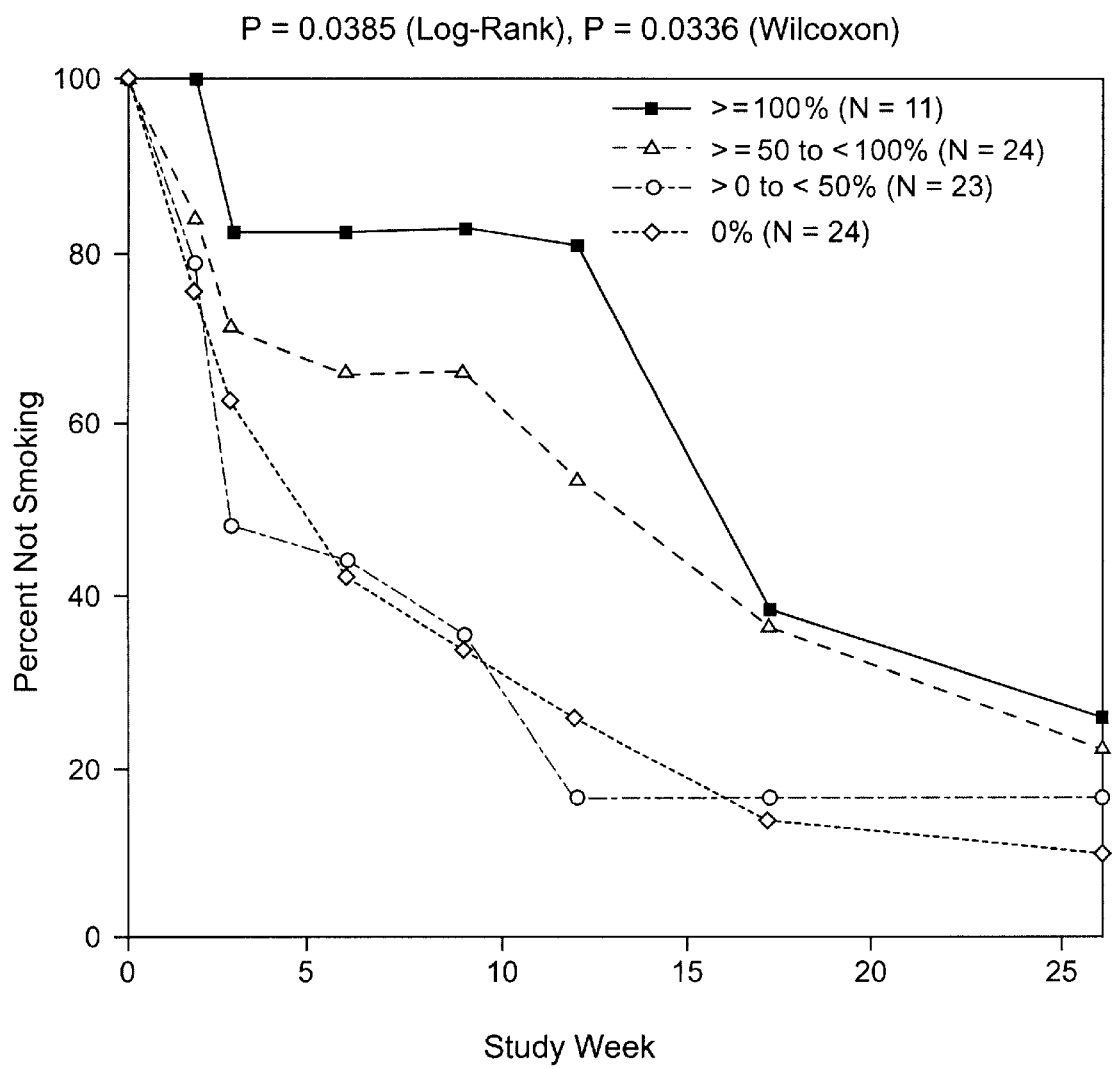

Of these 82 subjects, 24 patients had 0% cotinine replacement; 23 had a cotinine level from the nicotine patch >0% but <50% cotinine replacement; 24 subjects achieved cotinine replacement levels that were ≧50% but <100%; and 11 patients achieved cotinine replacement levels ≧100%. These results, shown by the survival curves in FIG. 8, are also significant (Wilcoxon P=0.034; log-rank P=0.039). This family of survival curves not only shows that those subjects achieving 100% cotinine replacement or higher did significantly better than those who achieved cotinine replacement levels between 50–100%; but also, that those patients who achieved less than 50% cotinine replacement from their patch dose did no better than those patients who were randomized to the placebo condition and had, in fact, 0% cotinine replacement.

FIG. 8 provides another important insight. Eighty percent of the smokers who achieved ≧100% cotinine replacement from their assigned nicotine patch dose were continuous nonsmokers through the six weeks of full nicotine patch treatment plus the second six weeks of tapering. In short, the survival curve had stayed steady and the risk of relapse had not increased at all. Then, within four weeks of stopping their nicotine patch dose, somewhat more than 50% relapsed, such that only 37.5% were continuous nonsmokers through the four-month follow-up point. This virtual, free-fall relapse continued over the next two months, so that only one-fourth were continuous nonsmokers for the entire six month period, or three months after stopping their nicotine patch dose. Since nearly half of these patients had been receiving 30 mg nicotine/16 hours during the first 6 weeks of treatment (Mean Nicotine Patch Dose=26.8±9.0 mg [±SD]), those subjects were then receiving 10mg nicotine/16 hours through weeks 9–12. (The mean dose during this last tapering phase was approximately 9 mg nicotine/16 hours).

The precipitous relapse after stopping all nicotine patch use after Week 12 would suggest that by a more gradual dosage reduction, relapse should be able to be substantially reduced, if not eliminated. This conclusion is also supported by the hazard analysis I carried out on our earlier nicotine patch study data-base and presented at the National Meeting of the Society of Behavioral Medicine (Sachs et al. Relapse Hazard Functions During and After Nicotine Patch Smoking Cessation Treatment. 15th National Scientific Meeting, Society Behavioral Medicine. Boston Mass., 1994).

Mann-Whitney Two-Sample Rank Test Analysis.

All randomized patients (N=91). Table 7 presents comparable data to that shown in FIG. 6. Here, however, the data are analyzed cross-sectionally using the Mann-Whitney Two-Sample Rank Test. Based on the dependent and independent variables used in this study, the Mann-Whitney Two-Sample Rank Test looks for an association between nonsmoking status and a higher level of cotinine replacement. In other words, it specifically looks for an orderly, dose-response type of effect. As Table 7 clearly shows, this orderly, dose-response effect was seen during the six weeks of treatment, during the subsequent six weeks of nicotine patch tapering (weeks 6–12), and even through the four-month follow-up visit, one month off all nicotine patches. The Mann-Whitney Two-Sample Rank Test was statistically significantly different (P<0.05, or better) at Week 6 (end of treatment) and through nicotine patch-dose tapering (Weeks 9 and 12).

TABLE 7

Percentage of Study Patients Continuously Not Smoking from Week 2 After Target Quit Date Through Week 26 (6 Months)* by Treatment Condition. All Randomized Patients (N = 91)

| | % Cotinine Replacement Condition | | | |
|---|---|---|---|---|
| Week | 0% (N = 31) | 50% (N = 29) | 100% (N = 31) | P-Value[1] |
| 2 | 64.5% | 82.8% | 83.9 | 0.0721 |
| 3 | 48.4% | 58.6% | 67.7% | 0.1244 |
| 6 | 32.3% | 55.2% | 63.3% | 0.0154 |
| 9 | 25.8% | 48.3% | 63.3% | 0.0034 |
| 12 | 19.4% | 34.6% | 50.0% | 0.0173 |
| 16 | 10.0% | 24.0% | 28.6% | 0.0874 |
| 26 | 6.9% | 24.0% | 11.1% | 0.4443 |

*Self-report of nonsmoking status objectively validated by CO ≦ 9 ppm.
[1]P-value computed by the Mann-Whitney Two-Sample Rank Test.

All randomized patients who could be adequately doses with three patches delivering up to 45 mg nicotine/16 hours (N=81). Table 8 presents data comparable to that shown in FIG. 7, looking only at those 81 subjects who could be adequately dosed by three nicotine patches delivering up 45 mg nicocotine/16 hours. Here the orderly, dose-response relationship is even more clearly seen and is significantly different through the fourth month of the study, or one month after all nicotine patch use had stopped (46% vs. 22% vs. 10% nonsmoking, for 100%, 50% and 0% Cot Repl conditions, respectively; P<0.02).

TABLE 8

Percentage of Study Patients Continuously Not Smoking from Week 2 After Target Quit Date Through Week 26 (6 Months)* by Treatment Condition. All Randomized Patients. (N = 91)

| | % Cotinine Replacement Condition | | | |
|---|---|---|---|---|
| Week | 0% (N = 31) | 50% (N = 27) | 100% (N = 23) | P-Value[1] |
| 2 | 64.5% | 81.5% | 87.0% | 0.0464 |
| 3 | 48.4% | 55.6% | 78.3% | 0.0343 |
| 6 | 32.3% | 51.9% | 72.7% | 0.0039 |
| 9 | 25.8% | 44.4% | 72.7% | 0.0009 |
| 12 | 19.4% | 29.2% | 62.5% | 0.0062 |
| 16 | 10.0% | 21.7% | 46.2% | 0.0124 |
| 26 | 6.9% | 21.7% | 20.0% | 0.1477 |

*Self-report of nonsmoking status objectively validated by CO ≦ 9 ppm.
[1]P-value computed by the Mann-Whitney 2-Sample Rank Test.

All patients by % cotinine replacement actually attained (N=82). Table 9 presents data comparable to that shown in FIG. 8, looking at the 82 subjects split into the four conditions, as described before, based on the % Cot Repl actually produced by their nicotine patch dose, irrespective of the treatment condition they were originally randomized to. Once again, an orderly, generally statistically significant, relationship emerges showing improved results with high % Cot Repl levels. Although not statistically significant after the end of the tapering phase (with the relatively small 82-subject sample size in this study), the trend would appear to be carried through one month and three months after stopping nicotine patch use.

TABLE 9

Percentage of Study Patients Continuously Not Smoking from Week 2 After Target Quit Date Through Week 26 (6 Months)* by Treatment Condition. All Patients by Cotinine Replacement Actually Attained. (N = 82)

| | % Cotinine Replacement Condition | | | | |
|---|---|---|---|---|---|
| Week | 0% (N = 24) | >0%–<50% (N = 23) | ≧50%–<100% (N = 24) | ≧100% (N = 11) | P-Value[1] |
| 2 | 75.0% | 78.3% | 83.3% | 100.0% | 0.1065 |
| 3 | 62.5% | 47.8% | 70.8% | 81.8% | 0.1933 |
| 6 | 41.7% | 43.5% | 65.2% | 81.8% | 0.0138 |
| 9 | 33.3% | 34.5% | 65.2% | 81.8% | 0.0019 |
| 12 | 25.0% | 15.8% | 52.6% | 80.0% | 0.0016 |
| 16 | 13.0% | 15.8% | 35.3% | 37.5% | 0.0566 |
| 26 | 9.1% | 15.8% | 21.4% | 25.0% | 0.2124 |

*Self-report of nonsmoking status objectively validated by CO ≦ 9 ppm.
[1]P-value computed by the Mann-Whitney Two-Sample Rank Test.

3. SAFETY

The only adverse event which occurred, despite delivering nicotine patch doses up to 45 mg nicotine/16 hours was mild itching and mild erythema at the patch application sites. There were no systemic side effects of any level of severity. Specifically there was no nausea, vomiting, diarrhea, tachycardia, sleep disturbance, insomnia or nightmares. There were no serious adverse events, such as myocardial infarction or any adverse events which required emergency room visits or hospitalization. In fact, no adverse events, either topical or systemic, that could be classified as moderate or severe, let along serious, occurred in any of the 91 patients in this study. The only adverse events which the subjects reported were the mild, topical, cutaneous side effects mentioned above.

4. EFFECTIVENESS OF HIGHER PERCENT COTININE REPLACEMENT IN RELATION TO BASELINE MEASUREMENTS OF TOBACCO DEPENDENCE

Another way to examine the potential benefits of the treatment conditions to which patients in this study were assigned is to use the data generated to examine the probability of being a continuous nonsmoker at specific time points, for example, week 6 (end of treatment) or week 12 (end of tapering phase), as a function of a specific baseline measurement of tobacco dependency. In this way, using a factor, or variable, which a physician could measure before even starting the patient's treatment, the physician could have an idea of how effective, for example, no treatment vs. 50% cotinine replacement by nicotine patch treatment vs. 100% cotinine replacement by nicotine patch treatment should be.

Two potential predictor variables were identified that a physician might easily and conveniently measure before commencing treatment: Fagerström Tolerance Questionnaire (FTQ) score and serum cotinine level, in ng/ml, while smoking. A logistic regression analysis on the data to examine these relationships is shown in FIGS. 9–12. Each figure is laid out in the same fashion, showing the relationship between the three conditions subjects might have been randomized to in this trial, placebo patch treatment, treatment with nicotine patch to achieve 50% replacement of the cotinine level that the patient had while smoking, or nicotine patch treatment to provide 100% Cot Repl.

Figure 9:
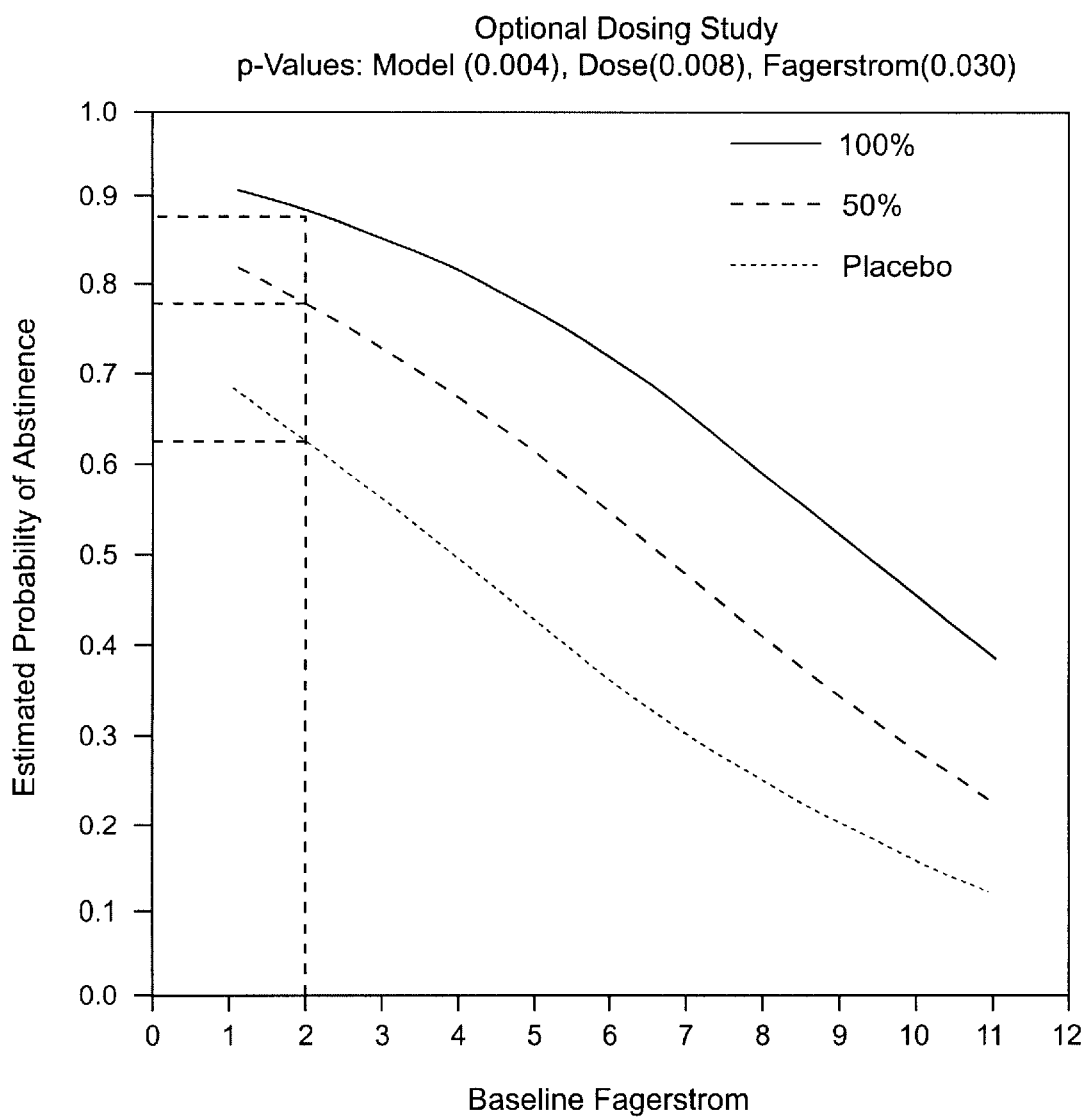

FIG. 9 illustrates that the data obtained in this study show that at the end of six weeks of treatment, if the patient with a FTQ score of two received no treatment other than office visits, then the probability of being a continuous nonsmoker was approximately 62%. In contrast, if the same patient, with a FTQ score of two, was provided a sufficient nicotine patch dose to replace 50% of the cotinine level obtained from cigarettes, then the probability of being a continuous nonsmoker for the first six weeks increased to approximately 78%, while the probability of being a continuous nonsmoker increased to nearly 90% if the patient was provided an even higher nicotine patch dose so that he or she replaced (in venous blood) 100% of the cotinine previously obtained from cigarette smoking. (Note vertical and horizontal dashed lines in FIG. 9). This improvement in smoking cessation rate is significant at P=0.008 (the P-value shown for the "Dose" under the title for FIG. 9).

If the smoker to be treated has a higher FTQ score (for example 11) then the probability of being a continuous nonsmoker for six weeks falls off rather sharply no matter what extent of nicotine patch treatment the patient might receive. The success rates are still significantly better, though, if the patient receives nicotine patch treatment, designed to individualize the dose, along with the office visits, rather than the office visits alone (placebo condition). A patient presenting for treatment with a FTQ score of 11 will have only a 10t chance of being a nonsmoker six weeks after stopping smoking if all he or she receives is regular office visits. In contrast this increases in an orderly, dose-response-fashion by four-fold, to nearly 40%, if the patient is provided an adequate nicotine patch dose to attain 100% replacement (in venous blood) in relation to the amount of cotinine attained while smoking cigarettes (P=0.008).

The P-values at the top of the figure show us the following: The higher the Fagerström score the lower the probability of quitting smoking; however, the physician can significantly and substantially improve upon the treatment outcome by adjusting the nicotine patch dose to increase the cotinine replacement level (P=0.004 for the overall model).

The Fagerström Tolerance Questionnaire score, measured while the patient is still smoking, is a powerful predictor of smoking status, but in an inverse fashion (Fagerström P=0.030). Finally, the Dose, or treatment condition, that the patient was randomized to in this study, is also a powerful, significant, and independent, predictor of treatment success, as shown by the Dose P=0.008: The higher the dose, or treatment condition, the better the treatment results.

Figure 10:
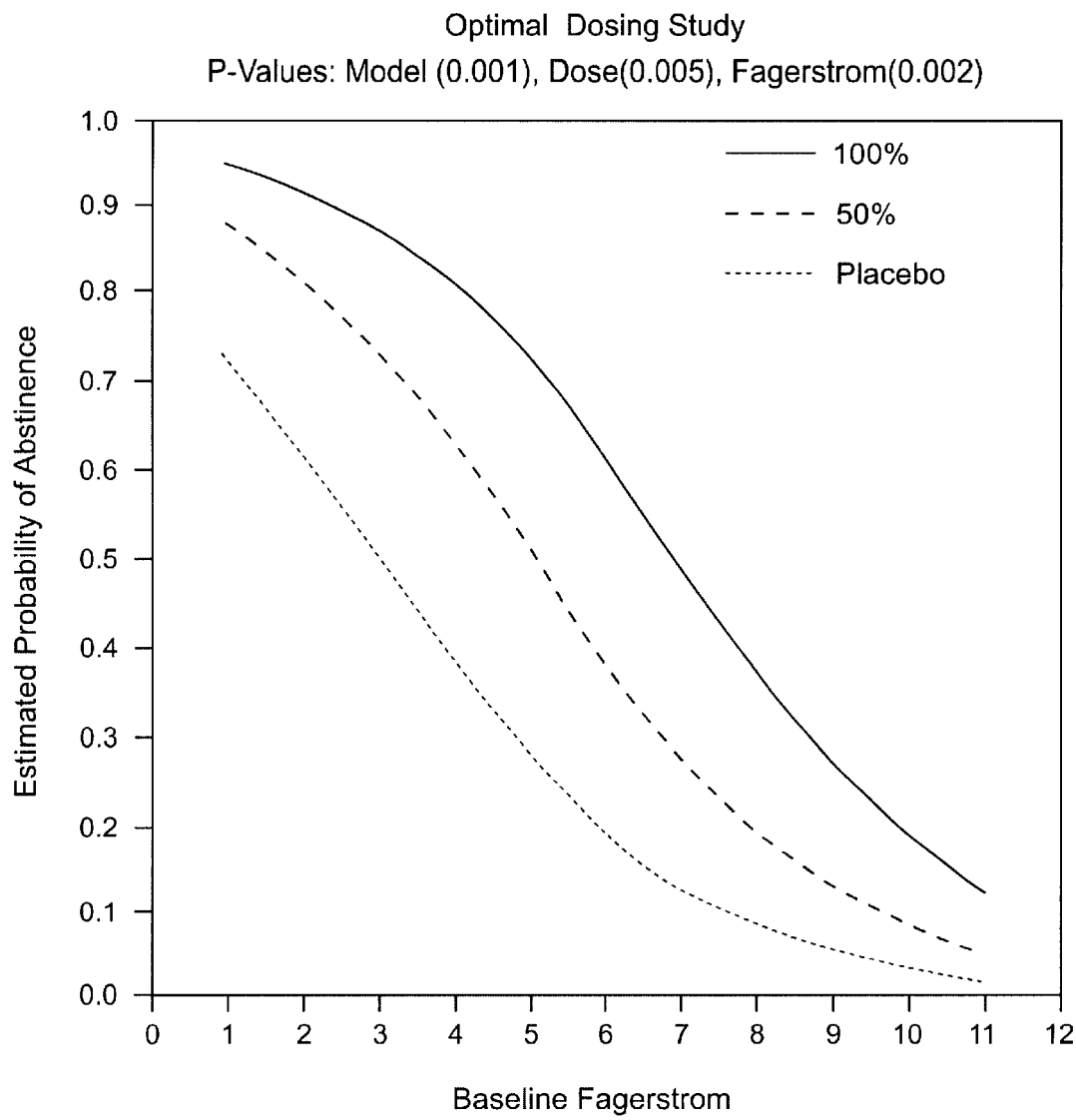

These same conclusions, with even more highly significant P-values for the probability of being a nonsmoker at week 12, the end of the six weeks of nicotine patch tapering, are shown in FIG. 10. In fact, FIG. 10 shows us that in the absence of a higher nicotine patch dose to achieve a higher nicotine replacement, the patient is virtually doomed to failure if he or she has a Fagerström score of 8, 9, 10, or 11, while the smoker with a FTQ score of 11 has only about a 10–15% chance of being a continuous nonsmoker for 12 weeks, even if given a nicotine patch dose providing 100% cotinine replacement, in relation to that cotinine level delivered by cigarettes. This is, though, nearly 10 times better than being treated only with physician office visits and no nicotine patches (about 2% quit rate). (This improvement in results shown by the Dose P=0.005.)

Figure 11:
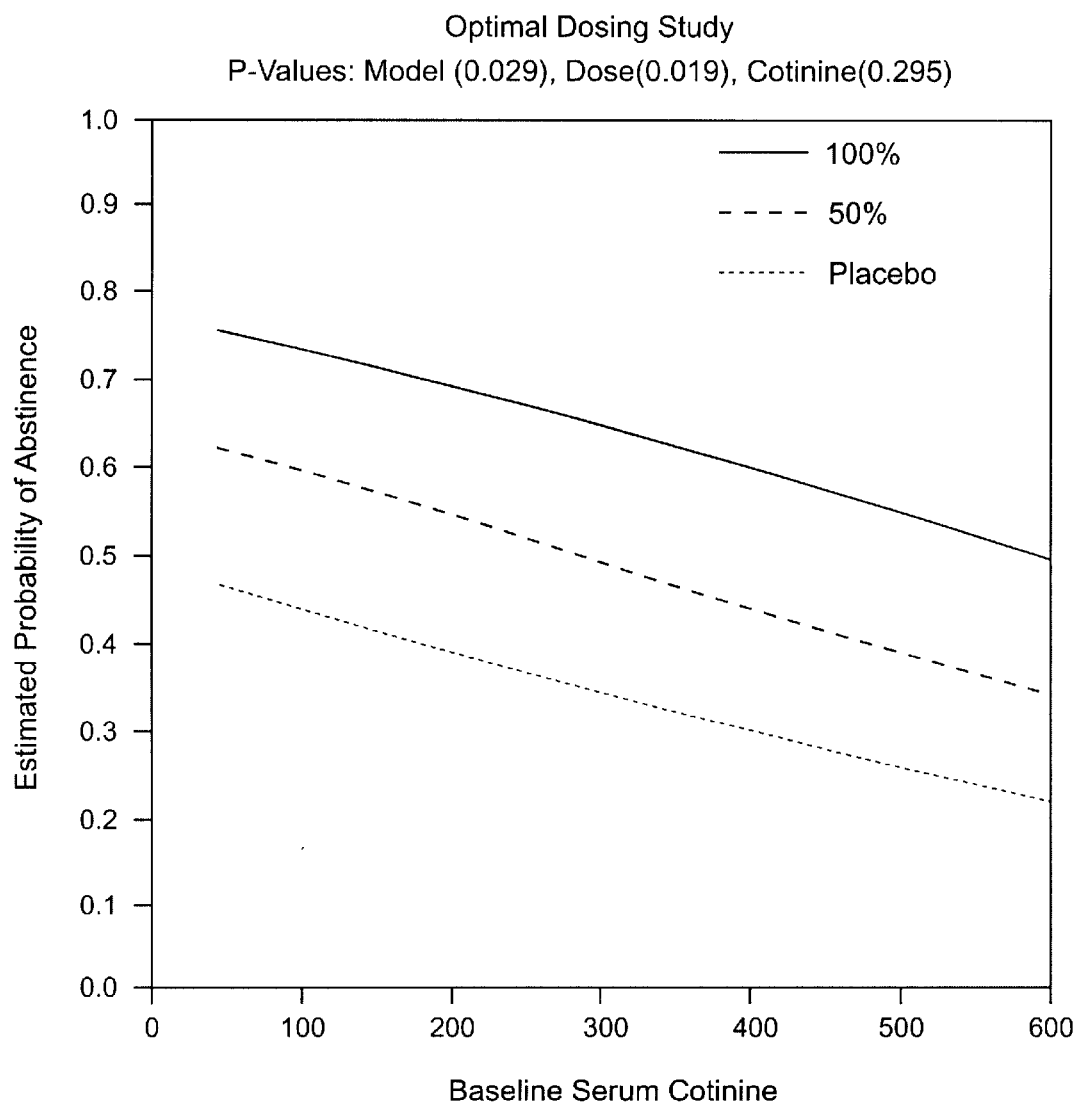
Figure 12:
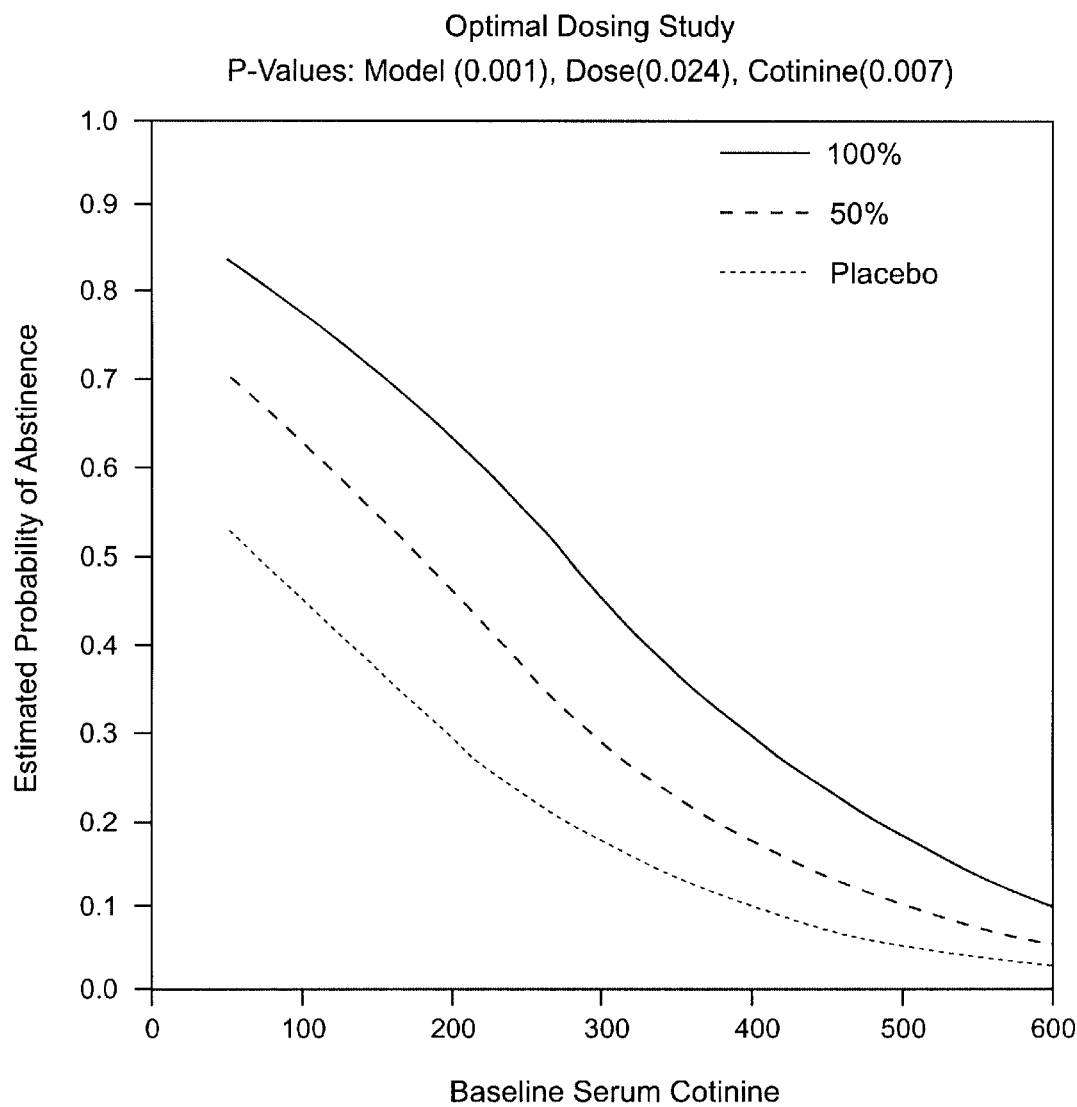

Another potential predictor variable that has recently been examined in the medical literature is the cotinine level (in ng/ml) while smoking cigarettes. The idea here, also, is that smokers who extract high levels of nicotine from their cigarettes have resultantly higher levels of cotinine in their blood (or saliva). Baseline serum cotinine levels while smoking cigarettes were measured. FIGS. 11 and 12 show the relationship between treatment condition (nicotine patch dose individually adjusted to achieve a target cotinine replacement level of 0% [placebo], 50%, or 100%), Baseline Serum Cotinine (in ng/ml), and smoking quit rates. The relationships are very similar to that seen in FIGS. 9 and 10 for the Fagerström nicotine dependency score. As with the Fagerström score, at the end of treatment (week 6), the overall model is highly significant (model P=0.029). While there is a clear trend that as the baseline serum cotinine level increases, the probability of being a nonsmoker at six weeks decreases, this did not reach statistical significance, however (Baseline Serum Cotinine P=0.295). Also, as with the data shown in FIG. 9, the higher the dose (% Cot Repl) the better the probability of continuously stopping smoking (Dose P=0.019).

For example, if a smoker has a baseline serum cotinine, measured while smoking cigarettes, of 300 ng/ml and is treated only with a series of regular office visits during the first six weeks (placebo condition), as done in this study, then the probability of being a continuous nonsmoker for six weeks is approximately 35%. If, on the other hand, in addition to receiving the same frequency and intensity of medical office visits, the patient also receives a sufficient nicotine patch dose to develop a cotinine level 100% of that achieved in venous blood while smoking cigarettes, then the probability of being a continuous nonsmoker virtually doubles to nearly 70% (P=0.019).

In contrast, however, at the end of nicotine patch tapering (week 12) all the relationships are highly statistically significant (see FIG. 12). The P-value for the overall model examining the relationship between nonsmoking, the baseline serum cotinine, and the nicotine patch dose necessary to achieve the target cotinine replacement level is highly significant at Model P=0.001. Similarly, the decreasing success rate as the baseline serum cotinine level increases is now highly significant with the Baseline Serum Cotinine P=0.007. Similarly, as was shown in FIG. 11 for the endof-treatment results (week 6), using an adequate nicotine patch dose to achieve a higher cotinine replacement level significantly and substantially increases nonsmoking rates for the entire 12-week period, regardless of the Baseline Serum-Cotinine level (Dose P=0.024). Although the results for all dosing levels are significantly and substantially higher if the subject is extracting less nicotine from cigarettes and, therefore, has a lower Baseline Serum Cotinine level while smoking cigarettes, the improvement in outcome results is statistically significant and also clinically meaningful and relevant, throughout the entire range of baseline serum cotinine levels encountered in this study. Moreover, this range of cigarette-produced, baseline serum cotinine levels is the range that is typically seen in research trials and in practice.

These four figures clearly show the considerable benefits to be gained by individualizing and adjusting nicotine patch dose to achieve a higher blood level during treatment. Not surprisingly, those who are less tobacco-dependent, whether measured by the Fagerström Tolerance Questionnaire score or by baseline blood cotinine levels, do better than those who are more highly dependent. Nonetheless, no matter what the tobacco dependency level, outcome results are substantially and significantly improved by increasing nicotine patch dose to increase-the cotinine replacement level.

6. RELATIONSHIP OF FTQ SCORE AT BASELINE AND % COTININE REPLACEMENT DURING TREATMENT AND TREATMENT EFFECTIVENESS

The data were analyzed in yet another and independent fashion. Specifically, survival data for all subjects whose serum cotinine, measured three days after starting patch treatment (Visit 0a), was provided by nicotine patches, i.e., the subjects who had not smoked during those first three days of nicotine patch treatment before their first serum cotinine level after beginning treatment was determined. Eighty-two patients across the three randomized treatment conditions (0% replacement, 50% replacement, and 100% replacement) had such "clean" cotinine measurements. The survival data were pooled for all 82 subjects, in effect disregarding which of the three treatment conditions a specific subject might have been initially randomized to, and created a pooled, or composite, survival curve. We then wanted to ascertain which of the three variables presented in the preceding analyses might predict survival—continuous smoking cessation—overall. To do this, we carried out the univariate, $\chi^2$ Wilcoxon Test. The three, potential, predictor variables that we included in this analysis were two measured at baseline, while the patients were still smoking, Fagerström Tolerance Questionnaire (FTQ) score and serum cotinine level in ng/ml. The third variable was the percentage cotinine replacement level actually achieved by nicotine patch treatment, expressed as a percentage replacement of the cotinine level achieved by cigarette smoking. Of these three variables, only the FTQ score and the percentage cotinine replacement were statistically significant ($\chi^2$=4.28, P=0.0386 and $\chi X^2$=5.61, P=0.0179, respectively). This analysis, also, showed that survival, or continuous smoking cessation, was directly related to cotinine replacement and inversely related to FTQ score. In other words, the higher the cotinine replacement, the longer the survival, or period of continuous abstinence; conversely, the higher the FTQ score, the shorter the survival, or time interval until relapse.

Forward, Stepwise Analysis.

The same three variables were again examined and, instead of looking at them independently, the three variables were examined to see if adding the second "strongest" variable to the first and the third "strongest" variable to the second+the first would improve the significance of the model. Thus, we started with that variable which had the smallest $\chi^2$ P-value, from the univariate analysis, adding the second strongest and the third strongest, in order. Thus, since the % Cot Repl during nicotine patch treatment had the smallest P-value (or the largest $\chi^2$ value) that variable was entered into the forward, stepwise analysis first. Since this was, however, basically a repeat of the univariate $\chi^2$ Wilcoxon Tests discussed above, that result was, of course, identical-$\chi$2=5.61 (P=0.0179). Next, the FTQ score, measured at baseline, was entered into the forward, stepwise Wilcoxon Model. Adding this improved the $\chi^2$ from 5.61 to 11.35, resulting in an overall P-value for the model of 0.0034. The incremental $\chi^2$ produced by adding the FTQ score measured at baseline to the % cotinine replacement achieved by nicotine patch treatment was 5.75 (incremental P=0.0165).

The third step was to add the serum cotinine level measured in venous blood at baseline, while the subjects were still smoking cigarettes, to see if that would improve the strength, or validity, of the model further. It did not. Adding the baseline cotinine only increased the $\chi^2$ of the total model from 11.35 to 11.59, but it reduced the $\chi^2$ P-value from 0.0034 to 0.0089. The incremental $\chi^2$ value produced by adding the baseline cotinine was trivial, at 0.24, with an insignificant incremental P-value of 0.6244. Consequently, this analysis indicates that the baseline cotinine would not be considered in such a model, only the % Cot Repl achieved by nicotine patch treatment+baseline FTQ score.

Note that adding the baseline FTQ score doubles the model's $\chi^2$ value and improves the P-value of the model by nearly a full order of magnitude. This indicates that FTQ score and resultant cotinine blood levels produced during nicotine patch treatment are independent predictor variables of survival, or smoking cessation success. If the FTQ score was measuring essentially the same thing as the % Cot Repl, then adding the FTQ score to the % Cot Repl in this forward, stepwise Wilcoxon Model would not have produced a larger $\chi^2$ value nor made the overall $\chi^2$ P-value for the model smaller. But it did. That the serum cotinine level measured at baseline, while patients were still smoking, worsened the $\chi^2$ P-value of the model, pulling it down to 0.0089, does not mean that the baseline cotinine level is not relevant. What it means is that the baseline cotinine level is measuring essentially the same thing as is measured by either the baseline FTQ score (likely) or the % Cot Repl achieved during treatment (also likely, since the cotinine replacement achieved during treatment is a function of the baseline cotinine), or both (most likely). Thus, adding the baseline cotinine measurement does not improve the predictive power of this model.

These conclusions further indicate that it will be possible to construct a four-dimensional model showing probability of stopping smoking in relation to the baseline FTQ score (which is, de facto, non-modifiable) and the 50% cotinine level achieved during treatment (which is most definitely modifiable and completely under physician and patient control) and time from target quit date. Second, knowing this, the physician should, in fact, be able to tailor the nicotine patch dose to achieve an optimal cotinine replacement level, as a direct function of the baseline FTQ score. The implication here is that patients with a lower FTQ score do not need as high a % Cot Repl to maximize their probability of stopping smoking as another patient who has a higher baseline FTQ score. For example, a patient with a FTQ score of only 2 may only need to be prescribed a nicotine patch dose sufficient to achieve a 50% Cot Repl replacement, to have an 80% chance of succeeding in stopping smoking. In contrast, another patient with a baseline FTQ score of 11 may need a much different nicotine patch dose, such that he or she is able to achieve a 175% Cot Repl in order to have the same probability of stopping smoking. That the physician can now respond in a rational, therapeutic way to treat patients with such easily and clearly identifiable pre-treatment differences, while standard practice for many areas of medical therapeutics, is a new and revolutionary finding for both diagnostic and therapeutic management of tobacco dependency.

To confirm this approach, the data from the present study were used to construct a four-dimensional model looking at precisely these relationships. The results, shown in the next section are dramatic and singularly impressive.

7. FOUR-DIMENSIONAL, DATABASED ANALYSIS PREDICTING SMOKING CESSATION OVER TIME FROM BASELINE FTQ SCORE AND % COTININE REPLACEMENT DURING TREATMENT

Step-wise, logistic regression analysis was performed to develop a series of models to enable prediction of abstinence over time. For the purposes of discussion herein, we shall present resultant equations and graphic models for six weeks, representing the end of treatment, and 12 weeks, representing the end of tapering. Based on our data reported in this study, the continuous six weeks abstinence proportion is shown by the following equation:

$$P_6 = 1/(1+e^{-\lambda}) \tag{4}$$

Where:

$P_6$=Fractional probability of being a nonsmoker for six continuous weeks;

e=The base of the natural logarithms; and $\lambda$=1.2342−0.2905 FTQ+0.0171% Cot Repl.

The P-value for the overall model is highly significant at P=0.0035, with the P-values for the Percentage Cotinine Replacement and FTQ being 0.0096 and 0.0342, respectively.

Equation 4 can then be solved for the desired cotinine replacement level to be achieved, given a desired probability, of 0 to 1.0, of being a nonsmoker and the patient's FTQ score, measured at baseline. Rearranging Equation 4, then, produces Equation 5:

$$X = \{-1.2342 + 0.2905 \text{ FTQ} + \ln [P_6/(1-P_6)]\}/0.0171 \tag{5}$$

Where

X=the percentage cotinine replacement level to be achieved by nicotine patch treatment, expressed as % Cot Repl as defined earlier in Equation 3;

FTQ Fagerström Tolerance Questionnaire score, ln=natural log, and $P_6$=Fractional probability of being, a nonsmoker for six continuous weeks.

Using a specific example, if a patient has a FTQ score of 7 and the % Cot Repl achieved was 180%, then entering those values into Equation 4 and solving for $P_6$ we get a 0.91, or 91% probability of being a continuous nonsmoker through Week 6. This is shown graphically in FIG. 13. This is based directly on the observed data from our study.

Alternatively, a practitioner could use this database and Equation 4 to answer the question: "What cotinine replacement level should be targeted a if the patient wants a 95% probability of being a nonsmoker for six weeks?" For the same patient, with a FTQ score=7, then solving Equation 5, the desired cotinine replacement level to be achieved by an adequate nicotine patch dose would be 220%. (A note of caution, this high of a cotinine replacement level exceeds any cotinine replacement levels actually observed in our database at this time. Thus, a final equation may be slightly different than presented above.)

A similar logistic equation was developed for 12-week, continuous abstinence as follows:

$$P_{12} = 1/(1+e^{-\lambda}) \tag{6}$$

Where:

$P_{12}$=Fractional probability of being a nonsmoker for 12 continuous weeks, e=The base of the natural logarithms, and $\lambda$=1.6767−0.5716 FTQ+0.0285 (% Cot Repl).

This equation has an overall P-value=0.0001, with P-values for the FTQ score and % Cot Repl of 0.0013 and 0.0007, respectively.

Rearranging this equation to enable computation of the desired serum cotinine replacement level to be achieved by nicotine patch treatment, produces Equation 7:

$$X = \{-1.6767 + 0.5716 \text{ FTQ} + \ln [P_{12}/(1-P_{12})]\}/0.0285 \tag{7}$$

Where:

X=the percentage cotinine replacement level to be achieved by nicotine patch treatment, expressed as % Cot Repl as defined earlier in Equation 3;

FTQ=Fagerström Tolerance Questionnaire score;

ln=natural log; and $P_{12}$=Fractional probability of being a nonsmoker for 12 continuous weeks.

Figure 14:
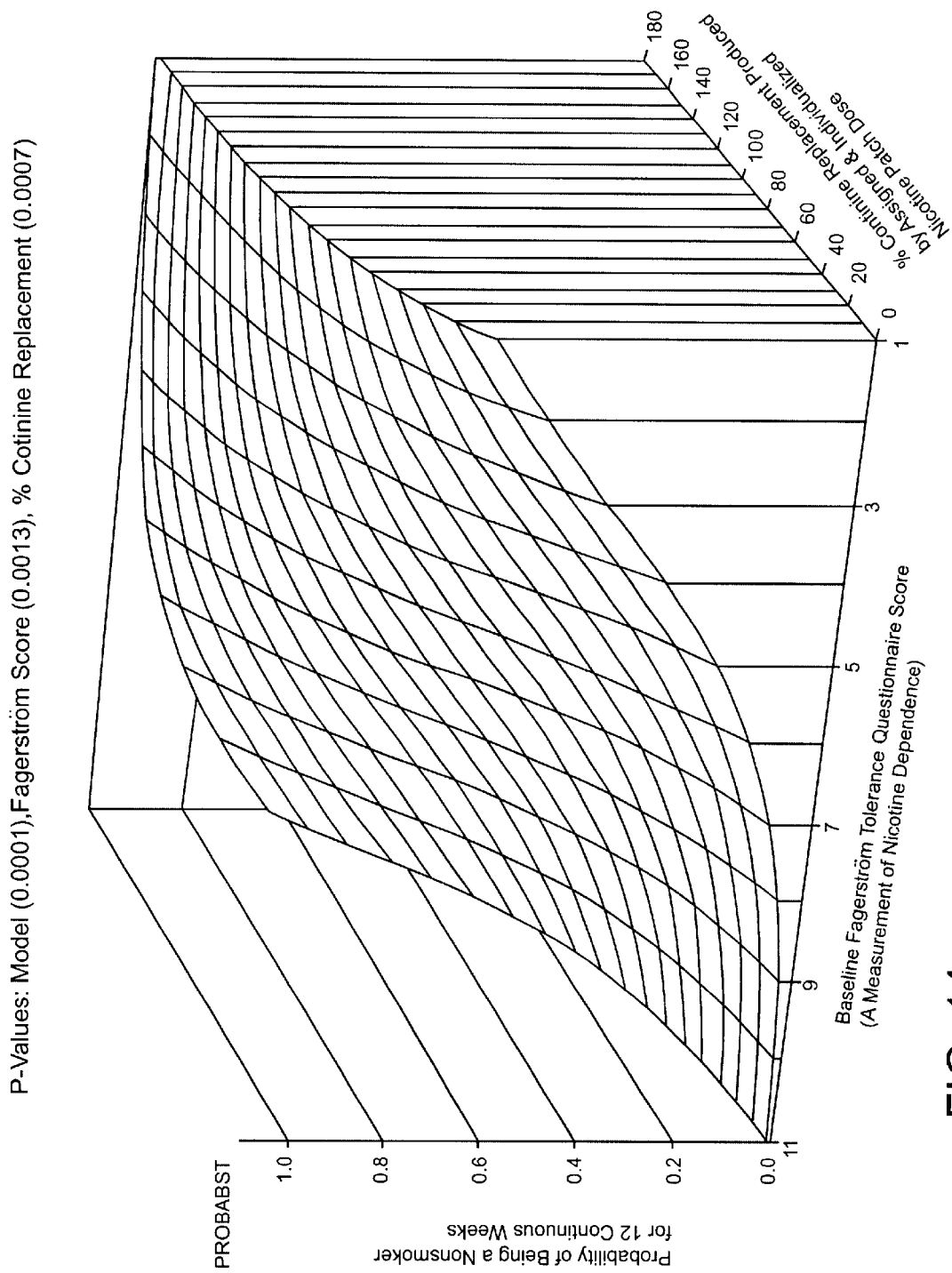

Equations 6 and 7 are shown by FIG. 14.

Figure 13:
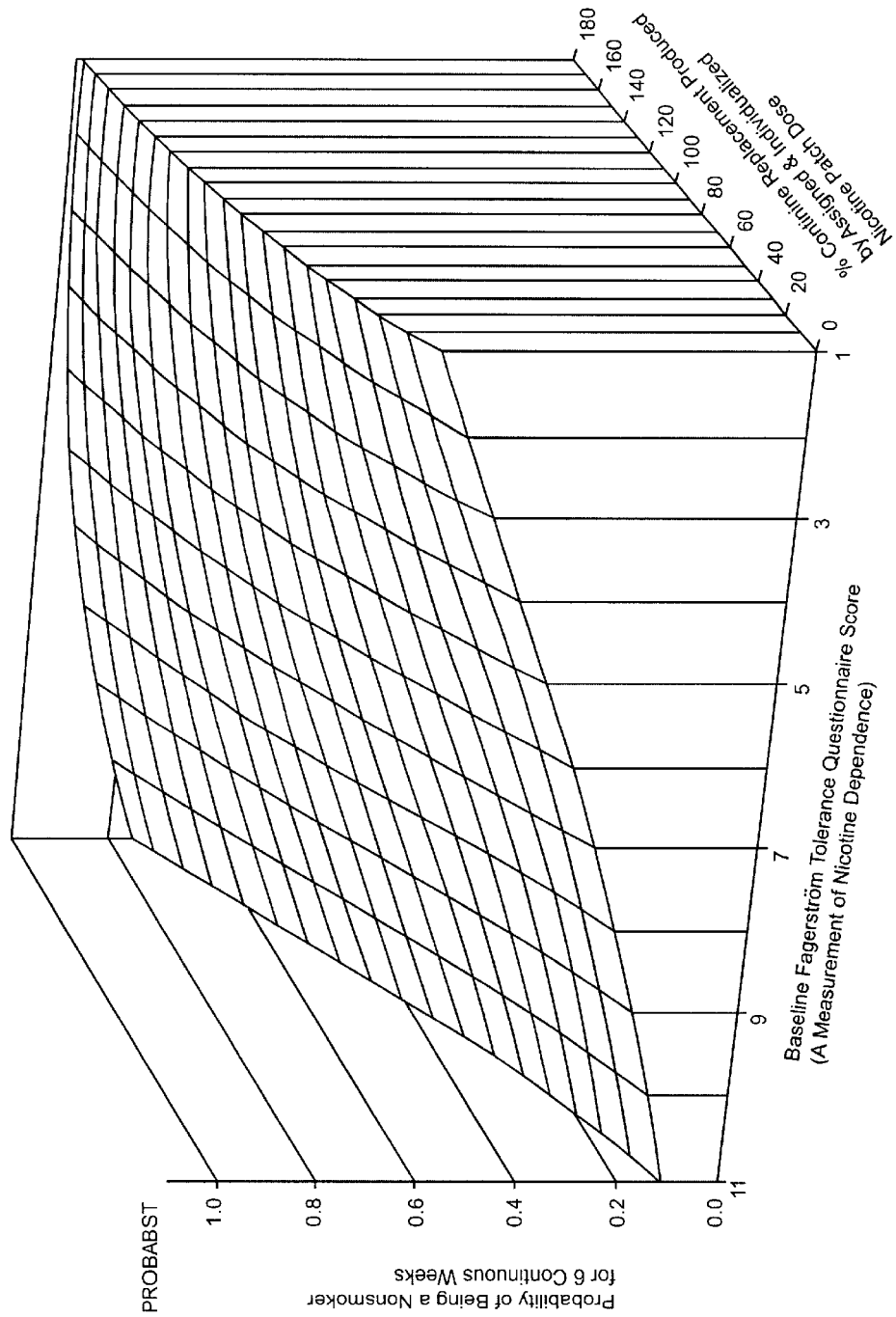

Thus, for the first time the clinician is provided with a tool to, with a high degree of confidence, at least within the boundary of the data ranges shown in FIGS. 13 and 14, individualize percentage cotinine replacement to achieve a desired probability of abstinence based on the patient's Fagerström score. This, then, translates directly to a target nicotine patch dose, using Equations 1 and 2, described earlier in this report (the Sachs Optimal Dosing Algorithm).

Although the foregoing invention has been described in detail for purposes of clarity of understanding, it will be obvious that certain modifications may be practiced within the scope of the appended claims.

What is claimed is:

1. A method for determining a nicotine dosage necessary to achieve a target nicotine serum concentration in an individual patient who is ceasing smoking, said method comprising:

(A) measuring a patient nicotine concentration while the patient is still smoking; and (B) determining the nicotine dosage as follows:

(i) for male patients:

determining the values of at least a body mass factor and a cumulative smoking factor; and determining the dosage to achieve the target nicotine serum concentration based on the patient's measured nicotine concentration, the body mass factor value, and the cumulative smoking factor value; or (ii) for female patients:

determining at least the value of a psychological dependence factor and age; and determining the dosage to achieve the target nicotine serum concentration based on the patient's measured nicotine concentration, the psychological dependence factor value and the age.

2. A method as in claim 1, wherein the target nicotine serum concentration is at least 40% of the smoking nicotine concentration.

3. A method as in claim 1, wherein the patient is a male, the body mass factor is a body mass index which is weight divided by height squared, and the cumulative smoking factor is the number of packs of cigarettes smoked per day immediately prior to cessation times the number of years smoked.

4. A method as in claim 3, further comprising determining a psychological dependence factor, which is measured using the Fagerström Tolerance Questionnaire, and determining the dosage based on the psychological dependence factor in addition to the other factors.

5. A method as in claim 4, further comprising determining age measured as years and determining the dosage based on age as well as the other factors.

6. A method as in claim 1, wherein the patient is a female and the psychological dependence factor is measured using the Fagerström Tolerance Questionnaire and age is measured as years.

7. A method as in claim 6, further comprising determining status, wherein no factor is introduced for pre-menopausal women and wherein a body mass factor is introduced for post-menopausal women.

8. A method as in claim 7, further comprising determining a body mass factor which is weight divided by height squared and determining the dosage based on the body mass factor as well as the other factor.

9. A method as in claim 1, wherein the patient nicotine level is measured as stable nicotine metabolite.

10. A method as in claim 1, wherein the nicotine dosage is a nicotine patch dosage.

* * * * *

UNITED STATES PATENT AND TRADEMARK OFFICE
CERTIFICATE OF CORRECTION

PATENT NO. : 6,602,892 B1
DATED : August 5, 2003
INVENTOR(S) : David P. L. Sachs It is certified that error appears in the above-identified patent and that said Letters Patent is hereby corrected as shown below:

Column 3
Line 36, "nicotine/16-hour intervals computed by the" should read -- nicotine/16-hour intervals, as computed by the --

Lines 38 and 39, "active, cotinine-replacement conditions of 50% (Fig.2) and 100% (Fig. 3 replacement, respectively" should read -- active cotinine-replacement conditions of 100% (Fig. 2) and 50% (Fig. 3). --

Lines 41-43, "cotinine replacement actually achieved by the nicotine patch dose replacement conditions computed by the algorithms of the present invention" should read -- cotinine-replacement actually achieved by each of the active cotinine-replacement conditions of 50% (Fig. 4)and 100% (Fig. 5), using the nicotine patch dose computed by the algorithms of the present invention. (NB: Scales on the ordinate and abscissa of these two graphs are different.) --

Lines 45-47, "is a graph comparing the percentage of patients who have continued not to smoke based on cotinine replacement levels of 100%, 50%, and 0%" should read -- compares the percentage of patients who had not smoked for 6 continuous months, based on the cotinine-replacement condition to which they had been randomized: 100%, 50%, and 0%. The initial nicotine patch dose had been computed for each patient using the algorithms of the present invention. --

Figure 6:
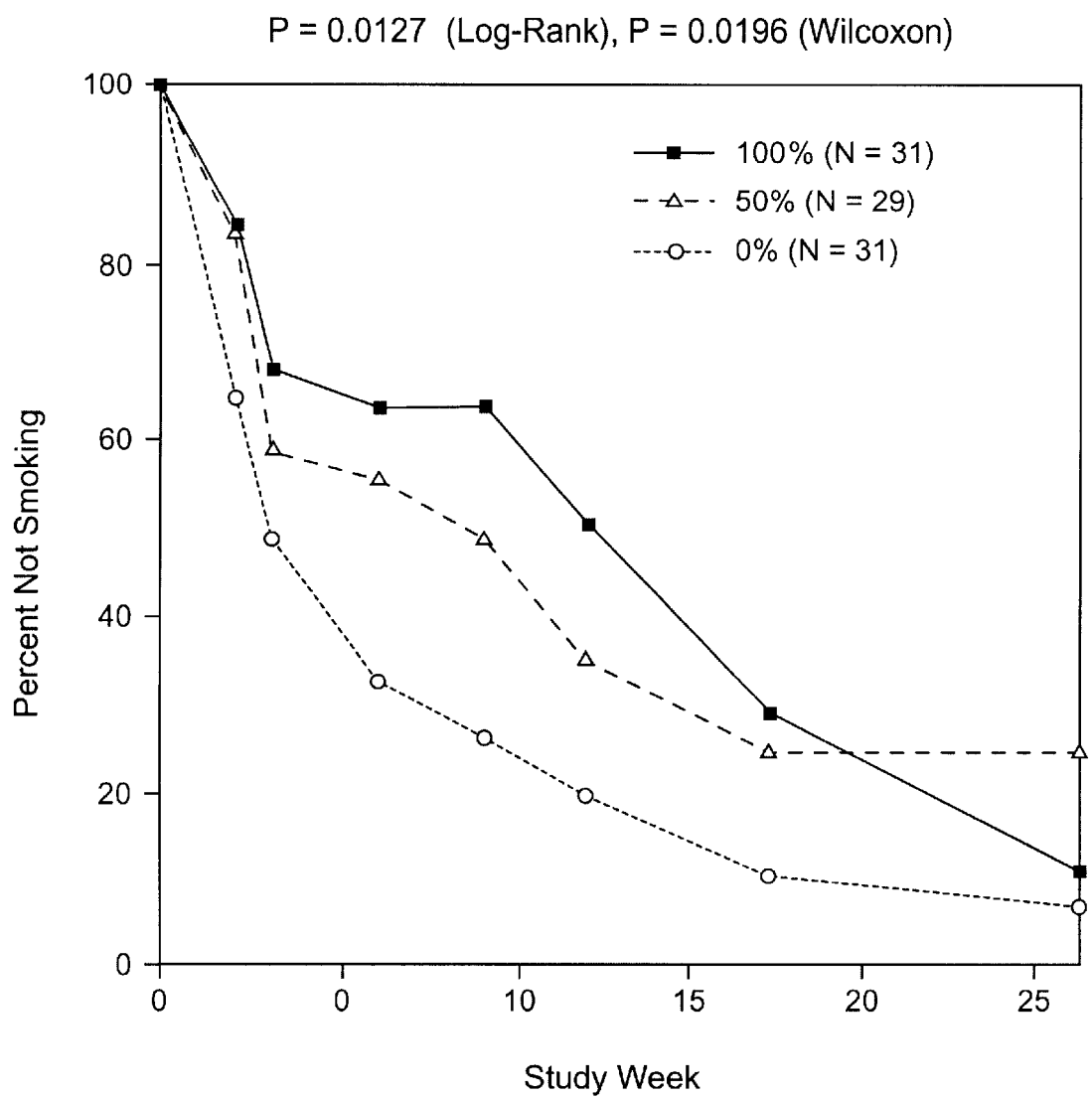

Lines 48-50, "Fig. 6 showing the percentage of patients who continued not smoking corrected to remove the underdosed subjects" should read -- Fig. 6, showing the percentage of patients who had not smoked for 6 continuous months, corrected to remove the 10, underdosed patients. --

Lines 51-53, "is a graph showing an alternative data plot of patients who continued not smoking based on different cotinine replacement percentages" should read -- shows an alternative data-plot of patients who had not smoked for 6 continuous months based on 1 of 4 cotinine-replacement-percentage groupings ( $\geq 100\%$, $\geq 50\%$ but $\leq 100\%$, $>0\%$ but $\leq 50\%$, or 0% [placebo] cotinine replacement) they had actually attained from their individualized, nicotine patch dose computed by the algorithms of the present invention. --

UNITED STATES PATENT AND TRADEMARK OFFICE
CERTIFICATE OF CORRECTION

PATENT NO. : 6,602,892 B1
DATED : August 5, 2003
INVENTOR(S) : David P. L. Sachs It is certified that error appears in the above-identified patent and that said Letters Patent is hereby corrected as shown below:

Column 3 (cont'd),
Lines 55-57, "is a graph plotting the likelihood of continued abstinence of patients based on both their Fagerstrom number and the percentage cotinine replacement level achieved" should read -- shows the probability of continued cigarette-abstinence for all patients through 6 weeks of individualized treatment, using the nicotine patch dose computed by the algorithms of the present invention, based on both their baseline, Fagerstrom Tolerance Questionnaire (FTQ) score and the cotinine-replacement condition to which they had been originally randomized. --

Lines 58-59, "is a plot similar to FIG. 9, shown with a different assumed dosage" should read -- is a graph similar to Fig. 9, but showing the probability of continued cigarette-abstinence for all patients, through 12 weeks of individualized treatment, using the individualized, nicotine patch dose computed by the algorithms of the present invention. --

Lines 60-62, "are plots of estimated probability of abstinence based on both their Fagerstrom number and the percentage cotinine replacement level achieved" should read -- show the probability of continued cigarette-abstinence for all patients through 6 weeks (Fig. 11) and 12 weeks (Fig. 12) of individualized treatment, using the nicotine patch dose computed by the algorithms of the present invention, based on baseline serum cotinine and the cotinine-replacement condition to which they had been originally randomized. --

Lines 63-64, "is a graph of data for patient having a FTQ score of 7 and a cotinine replacement of 180%" should read -- merges Figs. 9 and 11 into a 3-dimentional graph generated by Eq. 4 of the present invention. Fig. 13 plots the probability of continued cigarette-abstinence for all patients through 6 weeks of individualized treatment, based on both their baseline, Fagerstrom Tolerance Questionnaire (FTQ) score and the percentage continine-replacement that had been produced by the assigned and individualized nicotine patch dose, as computed by the algorithms of the present invention. --

UNITED STATES PATENT AND TRADEMARK OFFICE
CERTIFICATE OF CORRECTION

PATENT NO.    : 6,602,892 B1
DATED         : August 5, 2003
INVENTOR(S)   : David P. L. Sachs It is certified that error appears in the above-identified patent and that said Letters Patent is hereby corrected as shown below:

Column 3 (cont'd),
Lines 66-67, "is a plot of patient data based on equations 6 and 7 shown in the Experimental Section hereinbelow." should read -- merges Figs. 10 and 12 into a 3-dimensional graph generated by Eq. 6 of the present invention. Fig. 14 plots the probability of continued cigarette-abstinence for all patients through 12 weeks of individualized treatment, based on both their baseline, Fagerstrom Tolerance Questionnaire (FTQ) score and the percentage cotinine-replacement that had been produced by the assigned and individualized nicotine patch dose, as computed by the algorithms of the present inventions. --

Signed and Sealed this

Ninth Day of March, 2004

JON W. DUDAS
*Acting Director of the United States Patent and Trademark Office*